(12) United States Patent
Zhou et al.

(10) Patent No.: US 12,123,007 B2
(45) Date of Patent: Oct. 22, 2024

(54) **METHOD FOR CONSTRUCTING EFFICIENT *BACILLUS sUBTILIS* PROMOTER**

(71) Applicant: Jiangnan University, Wuxi (CN)

(72) Inventors: Zhemin Zhou, Wuxi (CN); Wenjing Cui, Wuxi (CN); Laichuang Han, Wuxi (CN); Zhongmei Liu, Wuxi (CN); Li Zhou, Wuxi (CN); Junling Guo, Wuxi (CN); Yu Yan, Wuxi (CN)

(73) Assignee: Jiangnan University, Wuxi (CN)

( * ) Notice: Subject to any disclaimer, the term of this patent is extended or adjusted under 35 U.S.C. 154(b) by 940 days.

(21) Appl. No.: 17/160,561

(22) Filed: Jan. 28, 2021

(65) Prior Publication Data

US 2021/0163962 A1    Jun. 3, 2021

Related U.S. Application Data

(63) Continuation of application No. PCT/CN2019/078816, filed on Mar. 20, 2019.

(30) Foreign Application Priority Data

Dec. 17, 2018 (CN) .......................... 201811542085.0

(51) Int. Cl.
*C12N 15/75* (2006.01)
(52) U.S. Cl.
CPC ........ *C12N 15/75* (2013.01); *C12N 2800/101* (2013.01); *C12N 2840/105* (2013.01)
(58) Field of Classification Search
CPC .............. C12N 15/75; C12N 2800/101; C12N 2840/105; C12N 15/113; C12P 21/00
See application file for complete search history.

(56) References Cited

U.S. PATENT DOCUMENTS 5,593,860 A    1/1997 Fischer

FOREIGN PATENT DOCUMENTS

CN    105505931 A    4/2016
CN    105779444 A    7/2016

OTHER PUBLICATIONS

McAllister (Journal of Biological Chemistry 263.24 (1988): 11743-11749) (Year: 1988).*
Zuber (Cold Spring Harbor symposia on quantitative biology. vol. 50. Cold Spring Harbor Laboratory Press, 1985) (Year: 1985).*
Chunlei GE et. al., "Efficient overexpression of recombinant Nattokinase in Bacillus subtilis by tandem promoters" Modern Food Science and Technology, 2016, v32 No. 11.
M.C. Magno-perez-bryan, et. al. "Comparative genomics within the Bacillus genus reveal the singularities of two robust Bacillus amyloliquefaciens biocontrol strains" Mol Plant Microbe Interact, Oct. 31, 2015, vol. 10 No. 28, p. 1102-1116.

* cited by examiner

*Primary Examiner* — Nancy J Leith
*Assistant Examiner* — Kyle T Rega
(74) *Attorney, Agent, or Firm* — IPRO, PLLC

(57) ABSTRACT

The present disclosure discloses a method for constructing an efficient *Bacillus subtilis* promoter, and belongs to the technical field of gene engineering. According to the present disclosure, natural promoters identified by different sigma subunits are connected in series to obtain some double-series and triple-series promoters, the lengths of intervening sequences between core areas of the promoters are optimized on the basis of series connection of the promoters to further improve the activity of the promoters, finally, different RBS designs are performed on the promoters, and it is verified that this strategy can not only improve the compatibility between the promoters and other gene expression regulating and controlling elements, but also controllably regulate the expression of exogenous genes. Through the method provided by the present disclosure, people can obtain the promoters with higher activity and stronger designability and compatibility through simple and convenient promoter design and modification methods. The method is simple and easy to implement and has wide application prospects in the construction of an exogenous protein efficient expression system and synthetic biology research.

16 Claims, 6 Drawing Sheets

Specification includes a Sequence Listing.

SEQUENCE LISTING

```
<160> NUMBER OF SEQ ID NOS: 110

<210> SEQ ID NO 1
<211> LENGTH: 60
<212> TYPE: DNA
<213> ORGANISM: Artificial Sequence
<220> FEATURE:
<223> OTHER INFORMATION: Synthetic DNA

<400> SEQUENCE: 1
aagcaaaaaa agtttgactc ggtattttaa ctatgttaat attgtaaaat gccaatgtat      60

<210> SEQ ID NO 2
<211> LENGTH: 60
<212> TYPE: DNA
<213> ORGANISM: Artificial Sequence
<220> FEATURE:
<223> OTHER INFORMATION: Synthetic DNA

<400> SEQUENCE: 2 gtttttttact attttgtgaa caatcaaggt agaatcaaat tgcaaacagt ggtaaaatat      60

<210> SEQ ID NO 3
<211> LENGTH: 60
<212> TYPE: DNA
<213> ORGANISM: Artificial Sequence
<220> FEATURE:
<223> OTHER INFORMATION: Synthetic DNA

<400> SEQUENCE: 3 ttaaaaata tattgacaac taactaaatt acctgttacc atgttcatca actgataaat      60

<210> SEQ ID NO 4
<211> LENGTH: 60
<212> TYPE: DNA
<213> ORGANISM: Artificial Sequence
<220> FEATURE:
<223> OTHER INFORMATION: Synthetic DNA

<400> SEQUENCE: 4
taaagtttaa atatttggat tttttaaata aagcgtttac aatatatgta gaaacaacaa      60

<210> SEQ ID NO 5
<211> LENGTH: 60
<212> TYPE: DNA
<213> ORGANISM: Artificial Sequence
```

```
<220> FEATURE:
<223> OTHER INFORMATION: Synthetic DNA

<400> SEQUENCE: 5
acaagataaa aacttgacag tgtcattaaa accgtgtaaa ctaagttatc gtaaagggat    60

<210> SEQ ID NO 6
<211> LENGTH: 60
<212> TYPE: DNA
<213> ORGANISM: Artificial Sequence
<220> FEATURE:
<223> OTHER INFORMATION: Synthetic DNA

<400> SEQUENCE: 6
ctcgttttaa ttgtctctaa aagcagttat gcggtactat catataaagg tccaatgttt    60

<210> SEQ ID NO 7
<211> LENGTH: 60
<212> TYPE: DNA
<213> ORGANISM: Artificial Sequence
<220> FEATURE:
<223> OTHER INFORMATION: Synthetic DNA

<400> SEQUENCE: 7
attttaaaaa cgagcaggat ttcagaaaaa atcgtggaat tgatacacta atgcttttat    60

<210> SEQ ID NO 8
<211> LENGTH: 60
<212> TYPE: DNA
<213> ORGANISM: Artificial Sequence
<220> FEATURE:
<223> OTHER INFORMATION: Synthetic DNA

<400> SEQUENCE: 8
atattaaaaa gaaaagcagg aatatagcaa ctccttagtg aatatagtaa aaatggaagg    60

<210> SEQ ID NO 9
<211> LENGTH: 60
<212> TYPE: DNA
<213> ORGANISM: Artificial Sequence
<220> FEATURE:
<223> OTHER INFORMATION: Synthetic DNA

<400> SEQUENCE: 9
aggccgagac gaataatagg aaaaaagtat gaatcaaacg aatctttttt cctccttctt    60

<210> SEQ ID NO 10
<211> LENGTH: 60
<212> TYPE: DNA
<213> ORGANISM: Artificial Sequence
<220> FEATURE:
<223> OTHER INFORMATION: Synthetic DNA

<400> SEQUENCE: 10
ttgagagatg agtaaaaagg attttatctt tttttgacga aatgagtatg ttgttgaggt    60

<210> SEQ ID NO 11
<211> LENGTH: 60
<212> TYPE: DNA
<213> ORGANISM: Artificial Sequence
<220> FEATURE:
<223> OTHER INFORMATION: Synthetic DNA

<400> SEQUENCE: 11
attttataaa aaaattgaaa cctttgaaa cgaagctcgt atacatacag accggtgaag    60
```

```
<210> SEQ ID NO 12
<211> LENGTH: 60
<212> TYPE: DNA
<213> ORGANISM: Artificial Sequence
<220> FEATURE:
<223> OTHER INFORMATION: Synthetic DNA

<400> SEQUENCE: 12
ctgtatgctt aagaatgaaa cctttctgta aaagagacgt ataaataacg acgaaaaaaa      60

<210> SEQ ID NO 13
<211> LENGTH: 60
<212> TYPE: DNA
<213> ORGANISM: Artificial Sequence
<220> FEATURE:
<223> OTHER INFORMATION: Synthetic DNA

<400> SEQUENCE: 13
tagtcccgtt ttatatgaaa ccttttttat tttagcccgt attaaaagta aattcagaga      60

<210> SEQ ID NO 14
<211> LENGTH: 60
<212> TYPE: DNA
<213> ORGANISM: Artificial Sequence
<220> FEATURE:
<223> OTHER INFORMATION: Synthetic DNA

<400> SEQUENCE: 14
tttatacata aaaaaatgaa acctttgata catttgttac gtatgaagag aaggcactta      60

<210> SEQ ID NO 15
<211> LENGTH: 60
<212> TYPE: DNA
<213> ORGANISM: Artificial Sequence
<220> FEATURE:
<223> OTHER INFORMATION: Synthetic DNA

<400> SEQUENCE: 15
aatattatta tggttaaaga aacttttttt attctatttc gtagtaaatt ttggaggtga      60

<210> SEQ ID NO 16
<211> LENGTH: 60
<212> TYPE: DNA
<213> ORGANISM: Artificial Sequence
<220> FEATURE:
<223> OTHER INFORMATION: Synthetic DNA

<400> SEQUENCE: 16
tttgtcttaa aattttgaaa cttttcccga ggtgtctcgt ataaatggta acggcagccg      60

<210> SEQ ID NO 17
<211> LENGTH: 120
<212> TYPE: DNA
<213> ORGANISM: Artificial Sequence
<220> FEATURE:
<223> OTHER INFORMATION: Synthetic DNA

<400> SEQUENCE: 17
aagcaaaaaa agtttgactc ggtattttaa ctatgttaat attgtaaaat gccaatgtat      60
attttaaaaa cgagcaggat ttcagaaaaa atcgtggaat tgatacacta atgcttttat     120

<210> SEQ ID NO 18
<211> LENGTH: 120
<212> TYPE: DNA
<213> ORGANISM: Artificial Sequence
```

```
<220> FEATURE:
<223> OTHER INFORMATION: Synthetic DNA

<400> SEQUENCE: 18
aagcaaaaaa agtttgactc ggtattttaa ctatgttaat attgtaaaat gccaatgtat      60
attttataaa aaaattgaaa cctttttgaaa cgaagctcgt atacatacag accggtgaag    120

<210> SEQ ID NO 19
<211> LENGTH: 120
<212> TYPE: DNA
<213> ORGANISM: Artificial Sequence
<220> FEATURE:
<223> OTHER INFORMATION: Synthetic DNA

<400> SEQUENCE: 19
attttaaaaa cgagcaggat ttcagaaaaa atcgtggaat tgatacacta atgcttttat      60
aagcaaaaaa agtttgactc ggtattttaa ctatgttaat attgtaaaat gccaatgtat    120

<210> SEQ ID NO 20
<211> LENGTH: 120
<212> TYPE: DNA
<213> ORGANISM: Artificial Sequence
<220> FEATURE:
<223> OTHER INFORMATION: Synthetic DNA

<400> SEQUENCE: 20
attttaaaaa cgagcaggat ttcagaaaaa atcgtggaat tgatacacta atgcttttat      60
attttataaa aaaattgaaa cctttttgaaa cgaagctcgt atacatacag accggtgaag    120

<210> SEQ ID NO 21
<211> LENGTH: 120
<212> TYPE: DNA
<213> ORGANISM: Artificial Sequence
<220> FEATURE:
<223> OTHER INFORMATION: Synthetic DNA

<400> SEQUENCE: 21
attttataaa aaaattgaaa cctttttgaaa cgaagctcgt atacatacag accggtgaag     60
aagcaaaaaa agtttgactc ggtattttaa ctatgttaat attgtaaaat gccaatgtat    120

<210> SEQ ID NO 22
<211> LENGTH: 120
<212> TYPE: DNA
<213> ORGANISM: Artificial Sequence
<220> FEATURE:
<223> OTHER INFORMATION: Synthetic DNA

<400> SEQUENCE: 22
attttataaa aaaattgaaa cctttttgaaa cgaagctcgt atacatacag accggtgaag     60
attttaaaaa cgagcaggat ttcagaaaaa atcgtggaat tgatacacta atgcttttat    120

<210> SEQ ID NO 23
<211> LENGTH: 180
<212> TYPE: DNA
<213> ORGANISM: Artificial Sequence
<220> FEATURE:
<223> OTHER INFORMATION: Synthetic DNA

<400> SEQUENCE: 23
aagcaaaaaa agtttgactc ggtattttaa ctatgttaat attgtaaaat gccaatgtat      60
attttaaaaa cgagcaggat ttcagaaaaa atcgtggaat tgatacacta atgcttttat    120
```
attttataaa aaaattgaaa cctttttgaaa cgaagctcgt atacatacag accggtgaag    180

```
<210> SEQ ID NO 24
<211> LENGTH: 180
<212> TYPE: DNA
<213> ORGANISM: Artificial Sequence
<220> FEATURE:
<223> OTHER INFORMATION: Synthetic DNA

<400> SEQUENCE: 24
```
aagcaaaaaa agtttgactc ggtattttaa ctatgttaat attgtaaaat gccaatgtat    60
attttataaa aaaattgaaa ccttttgaaa cgaagctcgt atacatacag accggtgaag    120
attttaaaaa cgagcaggat ttcagaaaaa atcgtggaat tgatacacta atgcttttat    180

```
<210> SEQ ID NO 25
<211> LENGTH: 180
<212> TYPE: DNA
<213> ORGANISM: Artificial Sequence
<220> FEATURE:
<223> OTHER INFORMATION: Synthetic DNA

<400> SEQUENCE: 25
```
attttaaaaa cgagcaggat ttcagaaaaa atcgtggaat tgatacacta atgcttttat    60
aagcaaaaaa agtttgactc ggtattttaa ctatgttaat attgtaaaat gccaatgtat    120
attttataaa aaaattgaaa ccttttgaaa cgaagctcgt atacatacag accggtgaag    180

```
<210> SEQ ID NO 26
<211> LENGTH: 180
<212> TYPE: DNA
<213> ORGANISM: Artificial Sequence
<220> FEATURE:
<223> OTHER INFORMATION: Synthetic DNA

<400> SEQUENCE: 26
```
attttaaaaa cgagcaggat ttcagaaaaa atcgtggaat tgatacacta atgcttttat    60
attttataaa aaaattgaaa ccttttgaaa cgaagctcgt atacatacag accggtgaag    120
aagcaaaaaa agtttgactc ggtattttaa ctatgttaat attgtaaaat gccaatgtat    180

```
<210> SEQ ID NO 27
<211> LENGTH: 180
<212> TYPE: DNA
<213> ORGANISM: Artificial Sequence
<220> FEATURE:
<223> OTHER INFORMATION: Synthetic DNA

<400> SEQUENCE: 27
```
attttataaa aaaattgaaa ccttttgaaa cgaagctcgt atacatacag accggtgaag    60
aagcaaaaaa agtttgactc ggtattttaa ctatgttaat attgtaaaat gccaatgtat    120
attttaaaaa cgagcaggat ttcagaaaaa atcgtggaat tgatacacta atgcttttat    180

```
<210> SEQ ID NO 28
<211> LENGTH: 180
<212> TYPE: DNA
<213> ORGANISM: Artificial Sequence
<220> FEATURE:
<223> OTHER INFORMATION: Synthetic DNA

<400> SEQUENCE: 28
```
attttataaa aaaattgaaa ccttttgaaa cgaagctcgt atacatacag accggtgaag    60
aagcaaaaaa agtttgactc ggtattttaa ctatgttaat attgtaaaat gccaatgtat    120

```
attttaaaaa cgagcaggat ttcagaaaaa atcgtggaat tgatacacta atgcttttat    180

<210> SEQ ID NO 29
<211> LENGTH: 135
<212> TYPE: DNA
<213> ORGANISM: Artificial Sequence
<220> FEATURE:
<223> OTHER INFORMATION: Synthetic DNA

<400> SEQUENCE: 29
aagcaaaaaa agtttgactc ggtatttttaa ctatgttaat attgtaaaat gccaatgtat    60 atttttcaa aaatattttt aaaaacgagc aggatttcag aaaaaatcgt ggaattgata    120
cactaatgct tttat                                                     135

<210> SEQ ID NO 30
<211> LENGTH: 150
<212> TYPE: DNA
<213> ORGANISM: Artificial Sequence
<220> FEATURE:
<223> OTHER INFORMATION: Synthetic DNA

<400> SEQUENCE: 30
aagcaaaaaa agtttgactc ggtatttttaa ctatgttaat attgtaaaat gccaatgtat    60
gtgtaactat atcctatttt ttcaaaaaat attttaaaaa cgagcaggat ttcagaaaaa    120
atcgtggaat tgatacacta atgcttttat                                     150

<210> SEQ ID NO 31
<211> LENGTH: 165
<212> TYPE: DNA
<213> ORGANISM: Artificial Sequence
<220> FEATURE:
<223> OTHER INFORMATION: Synthetic DNA

<400> SEQUENCE: 31
aagcaaaaaa agtttgactc ggtatttttaa ctatgttaat attgtaaaat gccaatgtat    60
ctttatgacc taattgtgta actatatcct attttttcaa aaatattttt aaaaacgagc    120
aggatttcag aaaaaatcgt ggaattgata cactaatgct tttat                    165

<210> SEQ ID NO 32
<211> LENGTH: 180
<212> TYPE: DNA
<213> ORGANISM: Artificial Sequence
<220> FEATURE:
<223> OTHER INFORMATION: Synthetic DNA

<400> SEQUENCE: 32
aagcaaaaaa agtttgactc ggtatttttaa ctatgttaat attgtaaaat gccaatgtat    60
tgcccgaaat gaaagcttta tgacctaatt gtgtaactat atcctatttt ttcaaaaaat    120
attttaaaaa cgagcaggat ttcagaaaaa atcgtggaat tgatacacta atgcttttat    180

<210> SEQ ID NO 33
<211> LENGTH: 195
<212> TYPE: DNA
<213> ORGANISM: Artificial Sequence
<220> FEATURE:
<223> OTHER INFORMATION: Synthetic DNA

<400> SEQUENCE: 33
aagcaaaaaa agtttgactc ggtatttttaa ctatgttaat attgtaaaat gccaatgtat    60
```

```
tttttattta ccttatgccc gaaatgaaag ctttatgacc taattgtgta actatatcct      120 atttttcaa aaatatttt aaaaacgagc aggatttcag aaaaaatcgt ggaattgata        180
cactaatgct tttat                                                      195

<210> SEQ ID NO 34
<211> LENGTH: 210
<212> TYPE: DNA
<213> ORGANISM: Artificial Sequence
<220> FEATURE:
<223> OTHER INFORMATION: Synthetic DNA

<400> SEQUENCE: 34
aagcaaaaaa agtttgactc ggtattttaa ctatgttaat attgtaaaat gccaatgtat       60
agagccggga tcactttttt atttaccta tgcccgaaat gaaagcttta tgacctaatt       120
gtgtaactat atcctatttt ttcaaaaaat attttaaaaa cgagcaggat ttcagaaaaa      180
atcgtggaat tgatacacta atgcttttat                                      210

<210> SEQ ID NO 35
<211> LENGTH: 195
<212> TYPE: DNA
<213> ORGANISM: Artificial Sequence
<220> FEATURE:
<223> OTHER INFORMATION: Synthetic DNA

<400> SEQUENCE: 35
attttataaa aaaattgaaa cctttgaaa cgaagctcgt atacatacag accggtgaag        60
gctattatat cataaaagca aaaaagttt gactcggtat tttaactatg ttaatattgt       120
aaaatgccaa tgtatatttt aaaaacgagc aggatttcag aaaaaatcgt ggaattgata     180
cactaatgct tttat                                                      195

<210> SEQ ID NO 36
<211> LENGTH: 210
<212> TYPE: DNA
<213> ORGANISM: Artificial Sequence
<220> FEATURE:
<223> OTHER INFORMATION: Synthetic DNA

<400> SEQUENCE: 36
attttataaa aaaattgaaa cctttgaaa cgaagctcgt atacatacag accggtgaag        60
ttcaaaaaaa gaaaggctat tatatcataa aagcaaaaaa agtttgactc ggtattttaa     120
ctatgttaat attgtaaaat gccaatgtat attttaaaaa cgagcaggat ttcagaaaaa     180
atcgtggaat tgatacacta atgcttttat                                      210

<210> SEQ ID NO 37
<211> LENGTH: 225
<212> TYPE: DNA
<213> ORGANISM: Artificial Sequence
<220> FEATURE:
<223> OTHER INFORMATION: Synthetic DNA

<400> SEQUENCE: 37
attttataaa aaaattgaaa cctttgaaa cgaagctcgt atacatacag accggtgaag        60
atgaagtttc cgtcgttcaa aaaagaaag gctattatat cataaaagca aaaaagttt       120 gactcggtat tttaactatg ttaatattgt aaaatgccaa tgtatatttt aaaaacgagc     180
aggatttcag aaaaaatcgt ggaattgata cactaatgct tttat                     225
```

<210> SEQ ID NO 38
<211> LENGTH: 240
<212> TYPE: DNA
<213> ORGANISM: Artificial Sequence
<220> FEATURE:
<223> OTHER INFORMATION: Synthetic DNA

<400> SEQUENCE: 38

```
attttataaa aaaattgaaa ccttttgaaa cgaagctcgt atacatacag accggtgaag      60
tcgaggaact gttcgatgaa gtttccgtcg ttcaaaaaaa gaaaggctat tatatcataa     120
aagcaaaaaa agtttgactc ggtattttaa ctatgttaat attgtaaaat gccaatgtat     180
attttaaaaa cgagcaggat ttcagaaaaa atcgtggaat tgatacacta atgcttttat     240
```

<210> SEQ ID NO 39
<211> LENGTH: 255
<212> TYPE: DNA
<213> ORGANISM: Artificial Sequence
<220> FEATURE:
<223> OTHER INFORMATION: Synthetic DNA

<400> SEQUENCE: 39

```
attttataaa aaaattgaaa ccttttgaaa cgaagctcgt atacatacag accggtgaag      60
ctgccattga aaagctcgag gaactgttcg atgaagtttc cgtcgttcaa aaaagaaag     120
gctattatat cataaaagca aaaaagttt gactcggtat tttaactatg ttaatattgt     180
aaaatgccaa tgtatatttt aaaaacgagc aggatttcag aaaaaatcgt ggaattgata     240
cactaatgct tttat                                                      255
```

<210> SEQ ID NO 40
<211> LENGTH: 270
<212> TYPE: DNA
<213> ORGANISM: Artificial Sequence
<220> FEATURE:
<223> OTHER INFORMATION: Synthetic DNA

<400> SEQUENCE: 40

```
attttataaa aaaattgaaa ccttttgaaa cgaagctcgt atacatacag accggtgaag      60
agcaaggcgc gccttctgcc attgaaaagc tcgaggaact gttcgatgaa gtttccgtcg     120
ttcaaaaaaa gaaaggctat tatatcataa aagcaaaaaa agtttgactc ggtattttaa     180
ctatgttaat attgtaaaat gccaatgtat attttaaaaa cgagcaggat ttcagaaaaa     240
atcgtggaat tgatacacta atgcttttat                                      270
```

<210> SEQ ID NO 41
<211> LENGTH: 195
<212> TYPE: DNA
<213> ORGANISM: Artificial Sequence
<220> FEATURE:
<223> OTHER INFORMATION: Synthetic DNA

<400> SEQUENCE: 41

```
attttataaa aaaattgaaa ccttttgaaa cgaagctcgt atacatacag accggtgaag      60
aagcaaaaaa agtttgactc ggtattttaa ctatgttaat attgtaaaat gccaatgtat     120
atttttcaa aaatatttt aaaaacgagc aggatttcag aaaaaatcgt ggaattgata     180
cactaatgct tttat                                                      195
```

<210> SEQ ID NO 42
<211> LENGTH: 210
<212> TYPE: DNA

<213> ORGANISM: Artificial Sequence
<220> FEATURE:
<223> OTHER INFORMATION: Synthetic DNA

<400> SEQUENCE: 42

| | |
|---|---|
| attttataaa aaaattgaaa ccttttgaaa cgaagctcgt atacatacag accggtgaag | 60 |
| aagcaaaaaa agtttgactc ggtatttttaa ctatgttaat attgtaaaat gccaatgtat | 120 |
| gtgtaactat atcctattt ttcaaaaaat attttaaaaa cgagcaggat ttcagaaaaa | 180 |
| atcgtggaat tgatacacta atgcttttat | 210 |

<210> SEQ ID NO 43
<211> LENGTH: 225
<212> TYPE: DNA
<213> ORGANISM: Artificial Sequence
<220> FEATURE:
<223> OTHER INFORMATION: Synthetic DNA

<400> SEQUENCE: 43

| | |
|---|---|
| attttataaa aaaattgaaa ccttttgaaa cgaagctcgt atacatacag accggtgaag | 60 |
| aagcaaaaaa agtttgactc ggtatttttaa ctatgttaat attgtaaaat gccaatgtat | 120 |
| ctttatgacc taattgtgta actatatcct attttttcaa aaatatttt aaaaacgagc | 180 |
| aggatttcag aaaaaatcgt ggaattgata cactaatgct tttat | 225 |

<210> SEQ ID NO 44
<211> LENGTH: 240
<212> TYPE: DNA
<213> ORGANISM: Artificial Sequence
<220> FEATURE:
<223> OTHER INFORMATION: Synthetic DNA

<400> SEQUENCE: 44

| | |
|---|---|
| attttataaa aaaattgaaa ccttttgaaa cgaagctcgt atacatacag accggtgaag | 60 |
| aagcaaaaaa agtttgactc ggtatttttaa ctatgttaat attgtaaaat gccaatgtat | 120 |
| tgcccgaaat gaaagcttta tgacctaatt gtgtaactat atcctattt ttcaaaaaat | 180 |
| attttaaaaa cgagcaggat ttcagaaaaa atcgtggaat tgatacacta atgcttttat | 240 |

<210> SEQ ID NO 45
<211> LENGTH: 255
<212> TYPE: DNA
<213> ORGANISM: Artificial Sequence
<220> FEATURE:
<223> OTHER INFORMATION: Synthetic DNA

<400> SEQUENCE: 45

| | |
|---|---|
| attttataaa aaaattgaaa ccttttgaaa cgaagctcgt atacatacag accggtgaag | 60 |
| aagcaaaaaa agtttgactc ggtatttttaa ctatgttaat attgtaaaat gccaatgtat | 120 |
| tttttattta ccttatgccc gaaatgaaag ctttatgacc taattgtgta actatatcct | 180 |
| attttttcaa aaatatttt aaaaacgagc aggatttcag aaaaaatcgt ggaattgata | 240 |
| cactaatgct tttat | 255 |

<210> SEQ ID NO 46
<211> LENGTH: 270
<212> TYPE: DNA
<213> ORGANISM: Artificial Sequence
<220> FEATURE:
<223> OTHER INFORMATION: Synthetic DNA

<400> SEQUENCE: 46

```
attttataaa aaaattgaaa ccttttgaaa cgaagctcgt atacatacag accggtgaag    60
aagcaaaaaa agtttgactc ggtattttaa ctatgttaat attgtaaaat gccaatgtat   120
agagccggga tcacttttt  atttaccta  tgcccgaaat gaaagcttta tgacctaatt   180
gtgtaactat atcctatttt ttcaaaaaat attttaaaaa cgagcaggat ttcagaaaaa   240
atcgtggaat tgatacacta atgcttttat                                    270
```

<210> SEQ ID NO 47
<211> LENGTH: 195
<212> TYPE: DNA
<213> ORGANISM: Artificial Sequence
<220> FEATURE:
<223> OTHER INFORMATION: Synthetic DNA

<400> SEQUENCE: 47

```
aagcaaaaaa agtttgactc ggtattttaa ctatgttaat attgtaaaat gccaatgtat    60
aaatttgata aacttatttt ataaaaaaat tgaaaccttt tgaaacgaag ctcgtataca   120
tacagaccgg tgaagatttt aaaaacgagc aggatttcag aaaaaatcgt ggaattgata   180
cactaatgct tttat                                                    195
```

<210> SEQ ID NO 48
<211> LENGTH: 210
<212> TYPE: DNA
<213> ORGANISM: Artificial Sequence
<220> FEATURE:
<223> OTHER INFORMATION: Synthetic DNA

<400> SEQUENCE: 48

```
aagcaaaaaa agtttgactc ggtattttaa ctatgttaat attgtaaaat gccaatgtat    60
tctacaccct gccaaaaatt tgataaactt attttataaa aaaattgaaa ccttttgaaa   120
cgaagctcgt atacatacag accggtgaag attttaaaaa cgagcaggat ttcagaaaaa   180
atcgtggaat tgatacacta atgcttttat                                    210
```

<210> SEQ ID NO 49
<211> LENGTH: 225
<212> TYPE: DNA
<213> ORGANISM: Artificial Sequence
<220> FEATURE:
<223> OTHER INFORMATION: Synthetic DNA

<400> SEQUENCE: 49

```
aagcaaaaaa agtttgactc ggtattttaa ctatgttaat attgtaaaat gccaatgtat    60
attcacgaat taccatctac accctgccaa aaatttgata aacttatttt ataaaaaaat   120
tgaaaccttt tgaaacgaag ctcgtataca tacagaccgg tgaagatttt aaaaacgagc   180
aggatttcag aaaaaatcgt ggaattgata cactaatgct tttat                   225
```

<210> SEQ ID NO 50
<211> LENGTH: 240
<212> TYPE: DNA
<213> ORGANISM: Artificial Sequence
<220> FEATURE:
<223> OTHER INFORMATION: Synthetic DNA

<400> SEQUENCE: 50

```
aagcaaaaaa agtttgactc ggtattttaa ctatgttaat attgtaaaat gccaatgtat    60
atgttaaggt agtttattca cgaattacca tctacaccct gccaaaaatt tgataaactt   120
```
attttataaa aaaattgaaa cctttgaaa cgaagctcgt atacatacag accggtgaag    180
attttaaaaa cgagcaggat ttcagaaaaa atcgtggaat tgatacacta atgctttat    240

<210> SEQ ID NO 51
<211> LENGTH: 255
<212> TYPE: DNA
<213> ORGANISM: Artificial Sequence
<220> FEATURE:
<223> OTHER INFORMATION: Synthetic DNA

<400> SEQUENCE: 51
aagcaaaaaa agtttgactc ggtattttaa ctatgttaat attgtaaaat gccaatgtat     60
aataatttta aaaatatgtt aaggtagttt attcacgaat taccatctac accctgccaa    120
aaatttgata aacttatttt ataaaaaaat tgaaaccttt tgaaacgaag ctcgtataca    180
tacagaccgg tgaagatttt aaaaacgagc aggatttcag aaaaaatcgt ggaattgata    240
cactaatgct tttat                                                    255

<210> SEQ ID NO 52
<211> LENGTH: 270
<212> TYPE: DNA
<213> ORGANISM: Artificial Sequence
<220> FEATURE:
<223> OTHER INFORMATION: Synthetic DNA

<400> SEQUENCE: 52
aagcaaaaaa agtttgactc ggtattttaa ctatgttaat attgtaaaat gccaatgtat     60
ctgttcagtc tgtataataa ttttaaaaat atgttaaggt agtttattca cgaattacca    120
tctacaccct gccaaaaatt tgataaactt attttataaa aaaattgaaa cctttgaaa    180 cgaagctcgt atacatacag accggtgaag attttaaaaa cgagcaggat ttcagaaaaa    240
atcgtggaat tgatacacta atgctttat                                     270

<210> SEQ ID NO 53
<211> LENGTH: 195
<212> TYPE: DNA
<213> ORGANISM: Artificial Sequence
<220> FEATURE:
<223> OTHER INFORMATION: Synthetic DNA

<400> SEQUENCE: 53
aagcaaaaaa agtttgactc ggtattttaa ctatgttaat attgtaaaat gccaatgtat     60
attttataaa aaaattgaaa cctttgaaa cgaagctcgt atacatacag accggtgaag    120
attttttcaa aaaatatttt aaaaacgagc aggatttcag aaaaaatcgt ggaattgata    180
cactaatgct tttat                                                    195

<210> SEQ ID NO 54
<211> LENGTH: 210
<212> TYPE: DNA
<213> ORGANISM: Artificial Sequence
<220> FEATURE:
<223> OTHER INFORMATION: Synthetic DNA

<400> SEQUENCE: 54
aagcaaaaaa agtttgactc ggtattttaa ctatgttaat attgtaaaat gccaatgtat     60
attttataaa aaaattgaaa cctttgaaa cgaagctcgt atacatacag accggtgaag    120
gtgtaactat atcctatttt ttcaaaaaat attttaaaaa cgagcaggat ttcagaaaaa    180
atcgtggaat tgatacacta atgctttat                                     210

<210> SEQ ID NO 55
<211> LENGTH: 225
<212> TYPE: DNA
<213> ORGANISM: Artificial Sequence
<220> FEATURE:
<223> OTHER INFORMATION: Synthetic DNA

<400> SEQUENCE: 55

```
aagcaaaaaa agtttgactc ggtattttaa ctatgttaat attgtaaaat gccaatgtat      60
attttataaa aaaattgaaa cctttttgaaa cgaagctcgt atacatacag accggtgaag    120
ctttatgacc taattgtgta actatatcct atttttttcaa aaaatatttt aaaaacgagc    180
aggatttcag aaaaaatcgt ggaattgata cactaatgct tttat                     225
```

<210> SEQ ID NO 56
<211> LENGTH: 240
<212> TYPE: DNA
<213> ORGANISM: Artificial Sequence
<220> FEATURE:
<223> OTHER INFORMATION: Synthetic DNA

<400> SEQUENCE: 56

```
aagcaaaaaa agtttgactc ggtattttaa ctatgttaat attgtaaaat gccaatgtat      60
attttataaa aaaattgaaa cctttttgaaa cgaagctcgt atacatacag accggtgaag    120
tgcccgaaat gaaagcttta tgacctaatt gtgtaactat atcctatttt ttcaaaaaat    180
attttaaaaa cgagcaggat ttcagaaaaa atcgtggaat tgatacacta atgctttttat   240
```

<210> SEQ ID NO 57
<211> LENGTH: 255
<212> TYPE: DNA
<213> ORGANISM: Artificial Sequence
<220> FEATURE:
<223> OTHER INFORMATION: Synthetic DNA

<400> SEQUENCE: 57

```
aagcaaaaaa agtttgactc ggtattttaa ctatgttaat attgtaaaat gccaatgtat      60
attttataaa aaaattgaaa cctttttgaaa cgaagctcgt atacatacag accggtgaag    120 tttttatttta ccttatgccc gaaatgaaag ctttatgacc taattgtgta actatatcct    180 atttttttcaa aaaatatttt aaaaacgagc aggatttcag aaaaaatcgt ggaattgata    240
cactaatgct tttat                                                      255
```

<210> SEQ ID NO 58
<211> LENGTH: 270
<212> TYPE: DNA
<213> ORGANISM: Artificial Sequence
<220> FEATURE:
<223> OTHER INFORMATION: Synthetic DNA

<400> SEQUENCE: 58

```
aagcaaaaaa agtttgactc ggtattttaa ctatgttaat attgtaaaat gccaatgtat      60
attttataaa aaaattgaaa cctttttgaaa cgaagctcgt atacatacag accggtgaag    120
agagccggga tcactttttt atttaccttta tgcccgaaat gaaagcttta tgacctaatt    180
gtgtaactat atcctatttt ttcaaaaaat attttaaaaa cgagcaggat ttcagaaaaa    240
atcgtggaat tgatacacta atgctttttat                                     270
```

<210> SEQ ID NO 59

<211> LENGTH: 210
<212> TYPE: DNA
<213> ORGANISM: Artificial Sequence
<220> FEATURE:
<223> OTHER INFORMATION: Synthetic DNA

<400> SEQUENCE: 59

```
aagcaaaaaa agtttgactc ggtatttaa ctatgttaat attgtaaaat gccaatgtat      60
atttataaa aaaattgaaa ccttttgaaa cgaagctcgt atacatacag accggtgaag     120
tctacaccct gccaaaaatt tgataaactt attttaaaaa cgagcaggat ttcagaaaaa    180
atcgtggaat tgatacacta atgcttttat                                      210
```

<210> SEQ ID NO 60
<211> LENGTH: 35
<212> TYPE: DNA
<213> ORGANISM: Artificial Sequence
<220> FEATURE:
<223> OTHER INFORMATION: Synthetic DNA

<400> SEQUENCE: 60

```
tcgaacatca tatttaaagt gccgctacac cacat                                35
```

<210> SEQ ID NO 61
<211> LENGTH: 35
<212> TYPE: DNA
<213> ORGANISM: Artificial Sequence
<220> FEATURE:
<223> OTHER INFORMATION: Synthetic DNA

<400> SEQUENCE: 61

```
tcgaacatca tatttaaagt cggagtactc cacat                                35
```

<210> SEQ ID NO 62
<211> LENGTH: 35
<212> TYPE: DNA
<213> ORGANISM: Artificial Sequence
<220> FEATURE:
<223> OTHER INFORMATION: Synthetic DNA

<400> SEQUENCE: 62

```
tcgaacatca tatttaaagt aggttcgttc cacat                                35
```

<210> SEQ ID NO 63
<211> LENGTH: 35
<212> TYPE: DNA
<213> ORGANISM: Artificial Sequence
<220> FEATURE:
<223> OTHER INFORMATION: Synthetic DNA

<400> SEQUENCE: 63

```
tcgaacatca tatttaaagt aaaggttacc cacat                                35
```

<210> SEQ ID NO 64
<211> LENGTH: 35
<212> TYPE: DNA
<213> ORGANISM: Artificial Sequence
<220> FEATURE:
<223> OTHER INFORMATION: Synthetic DNA

<400> SEQUENCE: 64

```
tcgaacatca tatttaaagt acgaggagtc cacat                                35
```

<210> SEQ ID NO 65
<211> LENGTH: 35

<210> SEQ ID NO 65
<211> LENGTH: 35
<212> TYPE: DNA
<213> ORGANISM: Artificial Sequence
<220> FEATURE:
<223> OTHER INFORMATION: Synthetic DNA

<400> SEQUENCE: 65
tcgaacatca tatttaaagt aataggagtc cacat                              35

<210> SEQ ID NO 66
<211> LENGTH: 35
<212> TYPE: DNA
<213> ORGANISM: Artificial Sequence
<220> FEATURE:
<223> OTHER INFORMATION: Synthetic DNA

<400> SEQUENCE: 66
tcgaacatca tatttaaagt aataggagtc cacat                              35

<210> SEQ ID NO 67
<211> LENGTH: 35
<212> TYPE: DNA
<213> ORGANISM: Artificial Sequence
<220> FEATURE:
<223> OTHER INFORMATION: Synthetic DNA

<400> SEQUENCE: 67
tcgaacatca tatttaaagt aaaggagtcc cacat                              35

<210> SEQ ID NO 68
<211> LENGTH: 35
<212> TYPE: DNA
<213> ORGANISM: Artificial Sequence
<220> FEATURE:
<223> OTHER INFORMATION: Synthetic DNA

<400> SEQUENCE: 68
tcgaacatca tatttaaagt agaggagggc cacat                              35

<210> SEQ ID NO 69
<211> LENGTH: 35
<212> TYPE: DNA
<213> ORGANISM: Artificial Sequence
<220> FEATURE:
<223> OTHER INFORMATION: 70

<400> SEQUENCE: 69
tcgaacatca tatttaaagt aaggaggttc cacat                              35

<210> SEQ ID NO 70
<211> LENGTH: 35
<212> TYPE: DNA
<213> ORGANISM: Artificial Sequence
<220> FEATURE:
<223> OTHER INFORMATION: Synthetic DNA

<400> SEQUENCE: 70
tcgaacatca tatttaaagt acaggaggtc cacat                              35

<210> SEQ ID NO 71
<211> LENGTH: 35
<212> TYPE: DNA
<213> ORGANISM: Artificial Sequence
<220> FEATURE:
<223> OTHER INFORMATION: Synthetic DNA

<400> SEQUENCE: 71
tcgaacatca tatttaaagt acaggaggtc cacat          35

<210> SEQ ID NO 72
<211> LENGTH: 35
<212> TYPE: DNA
<213> ORGANISM: Artificial Sequence
<220> FEATURE:
<223> OTHER INFORMATION: Synthetic DNA

<400> SEQUENCE: 72
tcgaacatca tatttaaagt aaaggaggtc cacat          35

<210> SEQ ID NO 73
<211> LENGTH: 69
<212> TYPE: DNA
<213> ORGANISM: Artificial Sequence
<220> FEATURE:
<223> OTHER INFORMATION: Synthetic DNA

<400> SEQUENCE: 73
cggtatttta actatgttaa tattgtaaaa tgccaatgta ttcgaacatc atatttaaag    60
tacgaggag                                                           69

<210> SEQ ID NO 74
<211> LENGTH: 62
<212> TYPE: DNA
<213> ORGANISM: Artificial Sequence
<220> FEATURE:
<223> OTHER INFORMATION: Synthetic DNA

<400> SEQUENCE: 74
acaatattaa catagttaaa ataccgagtc aaactttttt tgcttacctg ccctctgcca    60
cc                                                                  62

<210> SEQ ID NO 75
<211> LENGTH: 69
<212> TYPE: DNA
<213> ORGANISM: Artificial Sequence
<220> FEATURE:
<223> OTHER INFORMATION: Synthetic DNA

<400> SEQUENCE: 75
acaatcaagg tagaatcaaa ttgcaaacag tggtaaaata ttcgaacatc atatttaaag    60
tacgaggag                                                           69

<210> SEQ ID NO 76
<211> LENGTH: 62
<212> TYPE: DNA
<213> ORGANISM: Artificial Sequence
<220> FEATURE:
<223> OTHER INFORMATION: Synthetic DNA

<400> SEQUENCE: 76
ttgcaatttg attctacctt gattgttcac aaaatagtaa aaaacacctg ccctctgcca    60
cc                                                                  62

<210> SEQ ID NO 77
<211> LENGTH: 69
<212> TYPE: DNA
<213> ORGANISM: Artificial Sequence
<220> FEATURE:
<223> OTHER INFORMATION: Synthetic DNA

<400> SEQUENCE: 77
ttttttaaat aaagcgttta caatatatgt agaaacaaca atcgaacatc atatttaaag      60
tacgaggag                                                             69

<210> SEQ ID NO 78
<211> LENGTH: 62
<212> TYPE: DNA
<213> ORGANISM: Artificial Sequence
<220> FEATURE:
<223> OTHER INFORMATION: Synthetic DNA

<400> SEQUENCE: 78
atattgtaaa cgctttattt aaaaaatcca aatatttaaa ctttaacctg ccctctgcca      60
cc                                                                    62

<210> SEQ ID NO 79
<211> LENGTH: 69
<212> TYPE: DNA
<213> ORGANISM: Artificial Sequence
<220> FEATURE:
<223> OTHER INFORMATION: Synthetic DNA

<400> SEQUENCE: 79
gtgtcattaa aaccgtgtaa actaagttat cgtaaaggga ttcgaacatc atatttaaag      60
tacgaggag                                                             69

<210> SEQ ID NO 80
<211> LENGTH: 62
<212> TYPE: DNA
<213> ORGANISM: Artificial Sequence
<220> FEATURE:
<223> OTHER INFORMATION: Synthetic DNA

<400> SEQUENCE: 80
cttagtttac acggttttaa tgacactgtc aagtttttat cttgtacctg ccctctgcca      60
cc                                                                    62

<210> SEQ ID NO 81
<211> LENGTH: 69
<212> TYPE: DNA
<213> ORGANISM: Artificial Sequence
<220> FEATURE:
<223> OTHER INFORMATION: Synthetic DNA

<400> SEQUENCE: 81
aaagcagtta tgcggtacta tcatataaag gtccaatgtt ttcgaacatc atatttaaag      60
tacgaggag                                                             69

<210> SEQ ID NO 82
<211> LENGTH: 62
<212> TYPE: DNA
<213> ORGANISM: Artificial Sequence
<220> FEATURE:
<223> OTHER INFORMATION: Synthetic DNA

<400> SEQUENCE: 82
atatgatagt accgcataac tgcttttaga gacaattaaa acgagacctg ccctctgcca      60
cc                                                                    62

<210> SEQ ID NO 83
<211> LENGTH: 69
<212> TYPE: DNA

<213> ORGANISM: Artificial Sequence
<220> FEATURE:
<223> OTHER INFORMATION: Synthetic DNA

<400> SEQUENCE: 83
ctaactaaat tacctgttac catgttcatc aactgataaa ttcgaacatc atatttaaag    60
tacgaggag                                                            69

<210> SEQ ID NO 84
<211> LENGTH: 62
<212> TYPE: DNA
<213> ORGANISM: Artificial Sequence
<220> FEATURE:
<223> OTHER INFORMATION: Synthetic DNA

<400> SEQUENCE: 84
aacatggtaa caggtaattt agttagttgt caatatattt tttaaacctg ccctctgcca    60
cc                                                                   62

<210> SEQ ID NO 85
<211> LENGTH: 69
<212> TYPE: DNA
<213> ORGANISM: Artificial Sequence
<220> FEATURE:
<223> OTHER INFORMATION: Synthetic DNA

<400> SEQUENCE: 85
gattttatct tttttgacg aaatgagtat gttgttgagg ttcgaacatc atatttaaag     60
tacgaggag                                                            69

<210> SEQ ID NO 86
<211> LENGTH: 62
<212> TYPE: DNA
<213> ORGANISM: Artificial Sequence
<220> FEATURE:
<223> OTHER INFORMATION: Synthetic DNA

<400> SEQUENCE: 86
tcatttcgtc aaaaaaagat aaaatccttt ttactcatct ctcaaacctg ccctctgcca    60
cc                                                                   62

<210> SEQ ID NO 87
<211> LENGTH: 69
<212> TYPE: DNA
<213> ORGANISM: Artificial Sequence
<220> FEATURE:
<223> OTHER INFORMATION: Synthetic DNA

<400> SEQUENCE: 87
tttcagaaaa aatcgtggaa ttgatacact aatgctttta ttcgaacatc atatttaaag    60
tacgaggag                                                            69

<210> SEQ ID NO 88
<211> LENGTH: 62
<212> TYPE: DNA
<213> ORGANISM: Artificial Sequence
<220> FEATURE:
<223> OTHER INFORMATION: Synthetic DNA

<400> SEQUENCE: 88
tatcaattcc acgatttttt ctgaaatcct gctcgttttt aaaatacctg ccctctgcca    60
cc                                                                   62

<210> SEQ ID NO 89
<211> LENGTH: 69
<212> TYPE: DNA
<213> ORGANISM: Artificial Sequence
<220> FEATURE:
<223> OTHER INFORMATION: Synthetic DNA

<400> SEQUENCE: 89
gaatatagca actccttagt gaatatagta aaaatggaag gtcgaacatc atatttaaag    60
tacgaggag    69

<210> SEQ ID NO 90
<211> LENGTH: 62
<212> TYPE: DNA
<213> ORGANISM: Artificial Sequence
<220> FEATURE:
<223> OTHER INFORMATION: Synthetic DNA

<400> SEQUENCE: 90
atattcacta aggagttgct atattcctgc ttttcttttt aatatacctg ccctctgcca    60
cc    62

<210> SEQ ID NO 91
<211> LENGTH: 69
<212> TYPE: DNA
<213> ORGANISM: Artificial Sequence
<220> FEATURE:
<223> OTHER INFORMATION: Synthetic DNA

<400> SEQUENCE: 91 gaaaaagta tgaatcaaac gaatcttttt tcctccttct ttcgaacatc atatttaaag    60
tacgaggag    69

<210> SEQ ID NO 92
<211> LENGTH: 62
<212> TYPE: DNA
<213> ORGANISM: Artificial Sequence
<220> FEATURE:
<223> OTHER INFORMATION: Synthetic DNA

<400> SEQUENCE: 92
agattcgttt gattcatact tttttcctat tattcgtctc ggcctacctg ccctctgcca    60
cc    62

<210> SEQ ID NO 93
<211> LENGTH: 69
<212> TYPE: DNA
<213> ORGANISM: Artificial Sequence
<220> FEATURE:
<223> OTHER INFORMATION: Synthetic DNA

<400> SEQUENCE: 93 acctttgaa acgaagctcg tatacataca gaccggtgaa gtcgaacatc atatttaaag    60
tacgaggag    69

<210> SEQ ID NO 94
<211> LENGTH: 62
<212> TYPE: DNA
<213> ORGANISM: Artificial Sequence
<220> FEATURE:
<223> OTHER INFORMATION: Synthetic DNA

<400> SEQUENCE: 94
tgtatacgag cttcgtttca aaaggtttca attttttat aaaatacctg ccctctgcca    60
cc    62

<210> SEQ ID NO 95
<211> LENGTH: 69
<212> TYPE: DNA
<213> ORGANISM: Artificial Sequence
<220> FEATURE:
<223> OTHER INFORMATION: Synthetic DNA

<400> SEQUENCE: 95
acctttctgt aaagagacg tataaataac gacgaaaaaa atcgaacatc atatttaaag    60
tacgaggag    69

<210> SEQ ID NO 96
<211> LENGTH: 62
<212> TYPE: DNA
<213> ORGANISM: Artificial Sequence
<220> FEATURE:
<223> OTHER INFORMATION: Synthetic DNA

<400> SEQUENCE: 96
tttatacgtc tcttttacag aaaggtttca ttcttaagca tacagacctg ccctctgcca    60
cc    62

<210> SEQ ID NO 97
<211> LENGTH: 62
<212> TYPE: DNA
<213> ORGANISM: Artificial Sequence
<220> FEATURE:
<223> OTHER INFORMATION: Synthetic DNA

<400> SEQUENCE: 97
tttatacgtc tcttttacag aaaggtttca ttcttaagca tacagacctg ccctctgcca    60
cc    62

<210> SEQ ID NO 98
<211> LENGTH: 62
<212> TYPE: DNA
<213> ORGANISM: Artificial Sequence
<220> FEATURE:
<223> OTHER INFORMATION: Synthetic DNA

<400> SEQUENCE: 98
ttaatacggg ctaaaataaa aaaggtttca tataaaacgg gactaacctg ccctctgcca    60
cc    62

<210> SEQ ID NO 99
<211> LENGTH: 69
<212> TYPE: DNA
<213> ORGANISM: Artificial Sequence
<220> FEATURE:
<223> OTHER INFORMATION: Synthetic DNA

<400> SEQUENCE: 99
aacctttgat acatttgtta cgtatgaaga gaaggcactt atcgaacatc atatttaaag    60
tacgaggag    69

<210> SEQ ID NO 100
<211> LENGTH: 62

```
<212> TYPE: DNA
<213> ORGANISM: Artificial Sequence
<220> FEATURE:
<223> OTHER INFORMATION: Synthetic DNA

<400> SEQUENCE: 100
catacgtaac aaatgtatca aaggtttcat ttttttatgt ataaaacctg ccctctgcca      60
cc                                                                    62

<210> SEQ ID NO 101
<211> LENGTH: 69
<212> TYPE: DNA
<213> ORGANISM: Artificial Sequence
<220> FEATURE:
<223> OTHER INFORMATION: Synthetic DNA

<400> SEQUENCE: 101
aaactttttt tattctattt cgtagtaaat tttggaggtg atcgaacatc atatttaaag      60
tacgaggag                                                             69

<210> SEQ ID NO 102
<211> LENGTH: 62
<212> TYPE: DNA
<213> ORGANISM: Artificial Sequence
<220> FEATURE:
<223> OTHER INFORMATION: Synthetic DNA

<400> SEQUENCE: 102
actacgaaat agaataaaaa aagtttcttt aaccataata atattacctg ccctctgcca      60
cc                                                                    62

<210> SEQ ID NO 103
<211> LENGTH: 69
<212> TYPE: DNA
<213> ORGANISM: Artificial Sequence
<220> FEATURE:
<223> OTHER INFORMATION: Synthetic DNA

<400> SEQUENCE: 103
acttttcccg aggtgtctcg tataaatggt aacggcagcc gtcgaacatc atatttaaag      60
tacgaggag                                                             69

<210> SEQ ID NO 104
<211> LENGTH: 62
<212> TYPE: DNA
<213> ORGANISM: Artificial Sequence
<220> FEATURE:
<223> OTHER INFORMATION: Synthetic DNA

<400> SEQUENCE: 104
tttatacgag acacctcggg aaaagtttca aaatttaag acaaaacctg ccctctgcca       60
cc                                                                    62

<210> SEQ ID NO 105
<211> LENGTH: 66
<212> TYPE: DNA
<213> ORGANISM: Artificial Sequence
<220> FEATURE:
<223> OTHER INFORMATION: Synthetic DNA

<400> SEQUENCE: 105
cggtatttta actatgttaa tattgtaaaa tgccaatgta tattttaaaa acgagcagga      60
``` tttcag                                                          66

<210> SEQ ID NO 106
<211> LENGTH: 66
<212> TYPE: DNA
<213> ORGANISM: Artificial Sequence
<220> FEATURE:
<223> OTHER INFORMATION: Synthetic DNA

<400> SEQUENCE: 106
cggtatttta actatgttaa tattgtaaaa tgccaatgta tattttaaaa acgagcagga     60
tttcag                                                          66

<210> SEQ ID NO 107
<211> LENGTH: 62
<212> TYPE: DNA
<213> ORGANISM: Artificial Sequence
<220> FEATURE:
<223> OTHER INFORMATION: Synthetic DNA

<400> SEQUENCE: 107
tttcagaaaa aatcgtggaa ttgatacact aatgctttta taagcaaaaa aagtttgact     60
cg                                                              62

<210> SEQ ID NO 108
<211> LENGTH: 73
<212> TYPE: DNA
<213> ORGANISM: Artificial Sequence
<220> FEATURE:
<223> OTHER INFORMATION: Synthetic DNA

<400> SEQUENCE: 108
tttcagaaaa aatcgtggaa ttgatacact aatgctttta tattttataa aaaaattgaa     60
accttttgaa acg                                                  73

<210> SEQ ID NO 109
<211> LENGTH: 62
<212> TYPE: DNA
<213> ORGANISM: Artificial Sequence
<220> FEATURE:
<223> OTHER INFORMATION: Synthetic DNA

<400> SEQUENCE: 109
accttttgaa acgaagctcg tatacataca gaccggtgaa gaagcaaaaa aagtttgact     60
cg                                                              62

<210> SEQ ID NO 110
<211> LENGTH: 66
<212> TYPE: DNA
<213> ORGANISM: Artificial Sequence
<220> FEATURE:
<223> OTHER INFORMATION: Synthetic DNA

<400> SEQUENCE: 110
accttttgaa acgaagctcg tatacataca gaccggtgaa gattttaaaa acgagcagga     60
tttcag                                                          66

METHOD FOR CONSTRUCTING EFFICIENT *BACILLUS SUBTILIS* PROMOTER

REFERENCE TO SEQUENCE LISTING

The instant application contains a Sequence Listing in ASCII plain text file format as a file named "Seq.txt", created on Jan. 28, 2021, of 36,864 bytes in size, and which is hereby incorporated by reference in its entirety.

TECHNICAL FIELD

The present disclosure relates to a method for constructing an efficient *Bacillus subtilis* promoter, and belongs to the technical field of gene engineering.

BACKGROUND

*B. subtilis* is a gram positive type strain widely applied to exogenous protein expression, and it is widely applied to the aspect of industrial enzyme preparation production because of the ability to efficiently express exogenous proteins. However, currently-applied *B. subtilis* promoters, especially natural endogenous *B. subtilis* promoters (such as P43 promoters) are relatively low in activity and relatively poor in expression stability of exogenous genes, and this defect seriously restricts application of the *B. subtilis* to the field of efficient expression of the exogenous proteins. In order to overcome this defect, in recent years, on the one hand, people have used the idea of directed evolution to further screen and modify the natural promoters, and on the other hand, they have used the method of gene engineering and the idea of synthetic biology to construct synthetic promoters. Although the activity of the promoters can be greatly improved by modifying the natural promoters, some defects of the natural promoters still cannot be avoided, such as unstable expression and weak incompatibility with other expression regulating and controlling elements. Therefore, the construction of efficient and stable artificial promoters has huge application prospects in the aspect of breaking through the activity bottleneck of the natural promoters and improving the stability and compatibility of promoter elements.

At present, there are mainly two strategies for constructing the artificial promoters, one of the strategies is that the natural promoters are used as basic skeletons, the high-activity natural promoters are screened to be simplified, modified, rearranged and combined, and then new efficient artificial promoters including the natural promoter skeletons are constructed. The other strategy is that random DNA sequences of a certain length are fully artificially synthesized to be cloned to promoter screening vectors, and by virtue of a high-throughput screening device and a high-throughput screening method, the fully artificially synthesized sequences with promoter functions are screened out from the numerous random sequences to be used as promoter elements. Although both of the two strategies have significant disadvantages, the former relies on the high-activity natural promoters, people also need to have a deep understanding of the working principle of the promoters, and as for the series promoters, if the new promoters each include a plurality of repeated sequence fragments, the stability of the promoters and expression vectors will be adversely affected; and although the later does not need to deeply understand the working mechanism of the promoters, target promoters screened from the full random sequences need expensive high-throughput screening apparatuses, and the screening efficiency is low. Therefore, it is of great significance to provide a method for constructing an efficient and stable promoter for the efficient expression of the exogenous proteins.

SUMMARY

The first purpose of the present disclosure is to provide an element for regulating and controlling gene expression, which includes an artificial series promoter and a downstream RBS thereof, the artificial series promoter is formed by connecting at least two of promoters $P_{rpoB}$, $P_{spoVG}$ and $P_{sigW}$ in series and nucleotide sequences of the promoters $P_{rpoB}$, $P_{spoVG}$ and $P_{sigW}$ are respectively shown as SEQ ID NO:1, SEQ ID NO:7 and SEQ ID NO:11.

In one implementation of the present disclosure, a nucleotide sequence of the artificial series promoter is shown as any one of SEQ ID NO:17-SEQ ID NO:27.

In one implementation of the present disclosure, a nucleotide sequence of the artificial series promoter is shown as any one of SEQ ID NO: 29-SEQ ID NO:59.

In one implementation of the present disclosure, intervening sequences of 60 bp and 75 bp are respectively inserted between core areas of the promoters $P_{rpoB}$ and $P_{spoVG}$, and new promoters $P_{AW-D60}$ and $P_{AH-D75}$ shown as SEQ ID NO:32 and SEQ ID NO:33 are respectively obtained.

In one implementation of the present disclosure, intervening sequences of 45 bp and 75 bp are respectively inserted between core areas of the first two of the promoters $P_{sigW}$, $P_{rpoB}$ and $P_{spoVG}$, and new promoters $P_{WAH-D45}$ and $P_{WAH-D75}$ shown as SEQ ID NO:43 and SEQ ID NO:45 are respectively obtained.

In one implementation of the present disclosure, intervening sequences of 30 bp and 90 bp are respectively inserted between core areas of the first two of the promoters $P_{rpoB}$, $P_{sigW}$ and $P_{spoVG}$, and new promoters $P_{AWH-D30}$ and $P_{WAH-D90}$ shown as SEQ ID NO:54 and SEQ ID NO:58 are respectively obtained.

In one implementation of the present disclosure, a nucleotide sequence of the RBS is shown as any one of SEQ ID NO:60-72.

In one implementation of the present disclosure, an expression host of a target gene includes *B. subtilis*.

In one implementation of the present disclosure, the expression host of the target gene includes *B. subtilis* 168, *B. subtilis* WB400, *B. subtilis* WB600 or *B. subtilis* WB800.

In one implementation of the present disclosure, the target gene includes an exogenous gene or an endogenous gene.

In one implementation of the present disclosure, the target gene includes an enzyme gene or a non-enzyme gene.

The second purpose of the present disclosure is to provide a vector containing the above element.

The third purpose of the present disclosure is to provide a genetic engineering bacterium for expressing the above vector.

The fourth purpose of the present disclosure is to provide a method for regulating and controlling expression of a target gene in *B. subtilis*, and the above regulating and controlling element is co-expressed with the target gene.

In one implementation of the present disclosure, a target protein includes an enzyme.

In one implementation of the present disclosure, the *B. subtilis* includes *B. subtilis* 168, *B. subtilis* WB400, *B. subtilis* WB600 or *B. subtilis* WB800.

The fifth purpose of the present disclosure is to provide application of the above regulating and controlling element or genetic engineering bacterium to preparation of the target protein.

The sixth purpose of the present disclosure is to provide application of the above regulating and controlling element or genetic engineering bacterium to a field of food, pharmaceuticals or chemical engineering.

The present disclosure has the beneficial effects: the promoters identified by different sigma subunits are screened and characterized firstly in the present disclosure, promoters (recombinant plasmids containing different regulating and controlling elements are transformed into the *B. subtilis*, and the expression quantity of the target gene and the activity of the regulating and controlling elements are characterized by the fluorescence intensity of a culture solution cultured by recombinant bacteria) having the highest activity and identified by the subunits of sigA, sigH and sigW are selected therefrom, and through double series connection and triple series connection of the core areas, intervening sequence optimization of the core areas, RBS redesign and other modes, the regulating and controlling element with the activity being further improved is obtained.

The fluorescence intensities of $P_{AW-D60}$ and $P_{AH-D75}$ are respectively 0.94 time and 1.03 times higher than the fluorescence intensity of $P_{AW}$ (with the fluorescence intensity of 20262 a.u/$OD_{600}$) before modification; the fluorescence intensities (18245 a.u/$OD_{600}$) of $P_{WAH-D45}$ and $P_{WAH-D75}$ are respectively 0.87 time and 0.96 time higher than the fluorescence intensity of $P_{WAH}$ (with the fluorescence intensity of 10261 a.u/$OD_{600}$) before modification; and the fluorescence intensities of $P_{AWH-D30}$ and $P_{WAH-D90}$ are respectively 0.78 time and 0.78 time higher than the fluorescence intensity of $P_{AWH}$ (with the fluorescence intensity of 16879 a.u/$OD_{600}$) before modification.

When $P_{AH-D75}$ is combined with RBS11 (SEQ ID NO:70), the fluorescence intensity can reach 76216 a.u/$OD_{600}$ and is 0.85 time higher than that of $P_{AH-D75}$; when $P_{WAH-D75}$ is combined with RBS13 (SEQ ID NO:72), the fluorescence intensity can reach 77751 a.u/$OD_{600}$ and is 1.17 times higher than that of $P_{WAH-D75}$; and when $P_{AWH-D30}$ is combined with RBS13 (SEQ ID NO:72), the fluorescence intensity can reach 73781 a.u/$OD_{600}$ and is 1.45 times higher than that of $P_{AWH-D30}$.

Through the method provided by the present disclosure, people can obtain the promoters with the higher activity and stronger designability and compatibility through simple and convenient promoter design and modification methods. The method is simple and easy to implement and has wide application prospects in the construction of an exogenous protein efficient expression system and synthetic biology research.

DETAILED DESCRIPTION

1. A cloning method of a promoter: A primer including a promoter sequence is designed. An *Escherichia coli-B. subtilis* shuttle vector pB-sfGFP (i.e., pBSG03, a construction method is shown in Guan C, Cui W, Cheng J, et al. Construction and development of an auto-regulatory gene expression system in *Bacillus subtilis* [J]. Microbial Cell Factories, 2015, 14 (1): 150) with an sfGFP report gene (Genbank ID: AVR55189.1) is taken as a template. PrimeSTAR MAX DNA polymerase (purchased from Takara with an article number of R045Q) is used for full plasmid PCR. PCR procedures are: pre-denaturation at 98° C. for 1 min, circulation including denaturation at 98° C. for 30 s, annealing at 50° C. for 30 s, and extending at 72° C. for 1 min for a total of 30 times, and final extending at 72° C. for 10 min. Then, a plasmid template is digested and removed with a restriction enzyme DpnI to purify a PCR product. Then, fragments are cyclized through an Infusion reassembling method to be transformed into *E. coli* JM109 competent cells.

2. A detection method of an sfGFP fluorescence intensity: A sample is centrifuged at 12000×g for 2 min, and bacteria are collected, washed with PBS 3 times, and then diluted with PBS to a certain concentration to obtain a bacterium suspension. 200 μL of the bacterium suspension is taken to a 96-well ELISA plate, and the 96-well ELISA plate is placed into a Synergy™ H4 fluorescence microplate reader for fluorescence detection. Fluorescence is detected with excitation light of 485 nm and absorbed light of 528 nm.

3. A medium: LB medium (g·L$^{-1}$): 10 of Tryptone, 10 of NaCl, 5 of a yeast extract, pH 7.0, and 20 of agar powder added when a solid medium is prepared.

4. A transformation method of *B. subtilis* 168: Single colonies of the *B. subtilis* 168 are picked to be inoculated into a 2 mL SPI medium and subjected to shaking culture at 37° C. for 12-14 h. 100 μL of a culture is taken to be inoculated into a 5 mL SPI medium and subjected to shaking culture at 37° C. for 4-5 h, and then, $OD_{600}$ starts to be detected. When $OD_{600}$ is about 1.0, 200 μL of a bacterium solution is pipetted to be transferred into a 2 mL SPII medium and subjected to shaking incubation at 37° C. and 100 r·min$^{-1}$ for 1.5 h. 20 μL of a 100×EGTA solution is added into a tube to be cultured in a shaking table at 37° C. and 100 r·min$^{-1}$ for 10 min, and then each centrifuge tube of 1.5 mL is filled with 500 L of a mixture. A proper quantity of plasmids verified to be correct by sequencing are added into the tubes, and subjected to blowing-suction uniform mixing to be placed into the shaking table at 37° C. and 100 r·min$^{-1}$ for 2 h. Culture is completed, and about 200 μL of a bacterium solution is sucked to be uniformly smeared on a corresponding selective plate to be cultured at 37° C. for 12-14 h.

Figure 1:
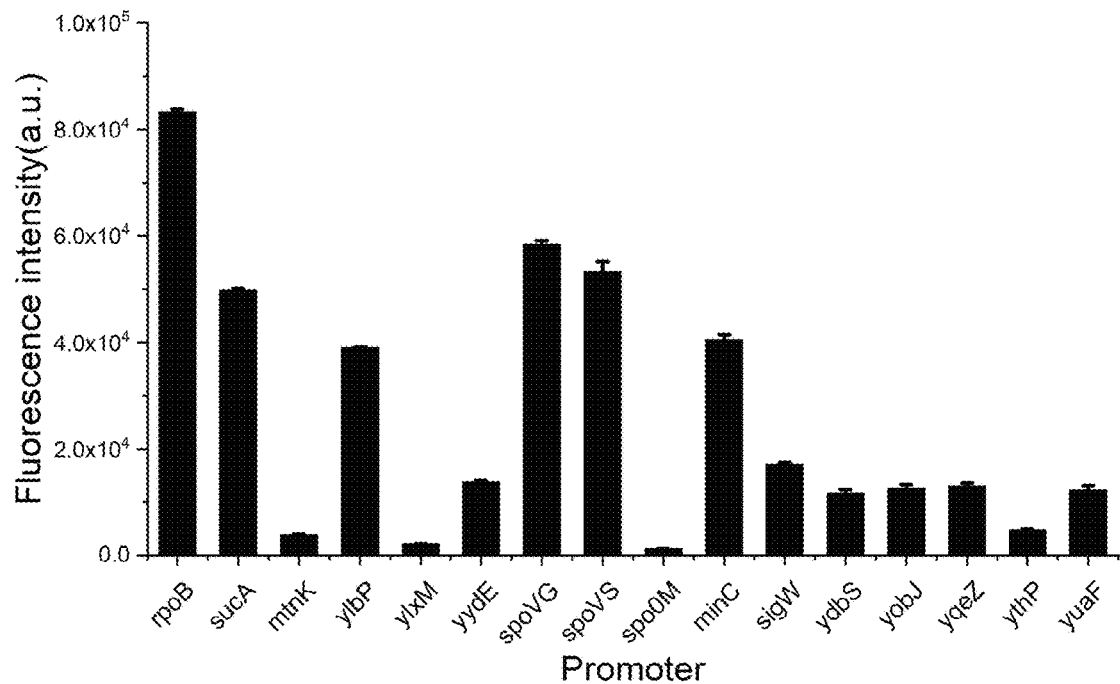
FIG. 1: screening and characterization of core areas of natural endogenous promoters identified by different sigma subunits.

Example 1: Cloning and Characterization of Single Promoters Identified by Different Sigma Subunits Promoters (with nucleotide sequences respectively shown as SEQ ID NO:1-SEQ ID NO:6) identified by six SigA subunits of $P_{rpoB}$, $P_{sucA}$, $P_{mtnK}$, $P_{ylbP}$, $P_{ylxM}$ and $P_{yydE}$, promoters (with nucleotide sequences respectively shown as SEQ ID NO: 7-SEQ ID NO: 10) identified by four SigH subunits of $P_{spoVG}$, $P_{pspoVS}$, $P_{spo0m}$ and $P_{minC}$ and promoters (with nucleotide sequences respectively shown as SEQ ID NO: 11-SEQ ID NO: 16) identified by six SigW subunits of $P_{sigW}$, $P_{ydbS}$, $P_{yobJ}$, $P_{yqeZ}$, $P_{ythP}$ and $P_{yuaF}$ are selected for testing. Core areas of the cloned promoters include −10 areas, −35 areas and transcriptional start sites (TSS) of the above promoters, with a total of 70 bp. To-be-screened-and-identified promoter sequences are designed on primers (shown in Table 2). The promoter sequences are introduced into a vector skeleton pB-sfGFP through a full plasmid PCR method, and then, through DpnI digestion, purification and assembly, cloned sfGFP expression plasmids containing the single promoters are transformed and constructed. The sfGFP expression plasmids for expressing the single promoters are transformed into strains of *B. subtilis* 168, and recombinant *B. subtilis* is constructed. The obtained recombinant *B. subtilis* is cultured in an LB medium at 37° C. and 200 rpm for 24 h, the expression level of sfGFP in bacteria is detected, and the degree of the activity of the promoters is judged through the intensity of an sfGFP fluorescence signal. The results are shown in FIG. 1 and Table 3, in the promoters identified by SigA, the $P_{rpoB}$ promoter has the highest activity, in the promoters indentified by SigH, $P_{spoVG}$ has the highest activity, and in the promoters identified by SigW, $P_{sigW}$ has the highest activity (FIG. 1).

TABLE 2

Cloning primers for single promoters

| Primer number | Sequence (5'-3')[a] | Sequence table number |
|---|---|---|
| $P_{rpoB}$-1 | CGGTATTTTAACTATGTTAATATTGTAAAATGCCAATGTATTCGAAC ATCATATTTAAAGTACGAGGAG | SEQ ID NO: 73 |
| $P_{rpoB}$-2 | ACAATATTAACATAGTTAAAATACCGAGTCAAACTTTTTTTGCTTAC CTGCCCTCTGCCACC | SEQ ID NO: 74 |
| $P_{sucA}$-1 | ACAATCAAGGTAGAATCAAATTGCAAACAGTGGTAAAATATTCGA ACATCATATTTAAAGTACGAGGAG | SEQ ID NO: 75 |
| $P_{sucA}$-2 | TTGCAATTTGATTCTACCTTGATTGTTCACAAAATAGTAAAAAACAC CTGCCCTCTGCCACC | SEQ ID NO: 76 |
| $P_{ylbP}$-1 | TTTTTTAAATAAAGCGTTTACAATATATGTAGAAACAACAATCGAA CATCATATTTAAAGTACGAGGAG | SEQ ID NO: 77 |
| $P_{ylbP}$-2 | ATATTGTAAACGCTTTATTTAAAAAATCCAAATATTTAAACTTTAAC CTGCCCTCTGCCACC | SEQ ID NO: 78 |
| $P_{ylxM}$-1 | GTGTCATTAAAACCGTGTAAACTAAGTTATCGTAAAGGGATTCGA ACATCATATTTAAAGTACGAGGAG | SEQ ID NO: 79 |
| $P_{ylxM}$-2 | CTTAGTTTACACGGTTTTAATGACACTGTCAAGTTTTTATCTTGTAC CTGCCCTCTGCCACC | SEQ ID NO: 80 |
| $P_{yydE}$-1 | AAAGCAGTTATGCGGTACTATCATATAAAGGTCCAATGTTTTCGAA CATCATATTTAAAGTACGAGGAG | SEQ ID NO: 81 |
| $P_{yydE}$-2 | ATATGATAGTACCGCATAACTGCTTTTAGAGACAATTAAAACGAGA CCTGCCCTCTGCCACC | SEQ ID NO: 82 |
| $P_{mtnK}$-1 | CTAACTAAATTACCTGTTACCATGTTCATCAACTGATAAATTCGAAC ATCATATTTAAAGTACGAGGAG | SEQ ID NO: 83 |
| $P_{mtnK}$-2 | AACATGGTAACAGGTAATTTAGTTAGTTGTCAATATATTTTTAAAC CTGCCCTCTGCCACC | SEQ ID NO: 84 |
| $P_{minC}$-1 | GATTTTATCTTTTTTTGACGAAATGAGTATGTTGTTGAGGTTCGAAC ATCATATTTAAAGTACGAGGAG | SEQ ID NO: 85 |
| $P_{minC}$-2 | TCATTTCGTCAAAAAAGATAAAATCCTTTTTACTCATCTCTCAAAC CTGCCCTCTGCCACC | SEQ ID NO: 86 |
| $P_{spoVG}$-1 | TTTCAGAAAAAATCGTGGAATTGATACACTAATGCTTTTATTCGAA CATCATATTTAAAGTACGAGGAG | SEQ ID NO: 87 |
| $P_{spoVG}$-2 | TATCAATTCCACGATTTTTTCTGAAATCCTGCTCGTTTTTAAAATACC TGCCCTCTGCCACC | SEQ ID NO: 88 |
| $P_{spoVS}$-1 | GAATATAGCAACTCCTTAGTGAATATAGTAAAAATGGAAGGTCGA ACATCATATTTAAAGTACGAGGAG | SEQ ID NO: 89 |

TABLE 2-continued

Cloning primers for single promoters

| Primer number | Sequence (5'-3')[a] | Sequence table number |
|---|---|---|
| $P_{spVS}$-2 | ATATTCACTAAGGAGTTGCTATATTCCTGCTTTTCTTTTTAATATACCTGCCCTCTGCCACC | SEQ ID NO: 90 |
| $P_{spo0M}$-1 | GAAAAAAGTATGAATCAAACGAATCTTTTTTTCCTCCTTCTTTCGAACATCATATTTAAAGTACGAGGAG | SEQ ID NO: 91 |
| $P_{spo0M}$-2 | AGATTCGTTTGATTCATACTTTTTTCCTATTATTCGTCTCGGCCTACCTGCCCTCTGCCACC | SEQ ID NO: 92 |
| $P_{sigW}$-1 | ACCTTTTGAAACGAAGCTCGTATACATACAGACCGGTGAAGTCGAACATCATATTTAAAGTACGAGGAG | SEQ ID NO: 93 |
| $P_{sigW}$-2 | TGTATACGAGCTTCGTTTCAAAAGGTTTCAATTTTTTTATAAAATACCTGCCCTCTGCCACC | SEQ ID NO: 94 |
| $P_{ydbS}$-1 | ACCTTTCTGTAAAAGAGACGTATAAATAACGACGAAAAAAATCGAACATCATATTTAAAGTACGAGGAG | SEQ ID NO: 95 |
| $P_{ydbS}$-2 | TTTATACGTCTCTTTTACAGAAAGGTTTCATTCTTAAGCATACAGACCTGCCCTCTGCCACC | SEQ ID NO: 96 |
| $P_{yobJ}$-1 | ACCTTTTTTATTTTAGCCCGTATTAAAAGTAAATTCAGAGATCGAACATCATATTTAAAGTACGAGGAG | SEQ ID NO: 97 |
| $P_{yobJ}$-2 | TTAATACGGGCTAAAATAAAAAAGGTTTCATATAAAACGGGACTAACCTGCCCTCTGCCACC | SEQ ID NO: 98 |
| $P_{yqeZ}$-1 | AACCTTTGATACATTTGTTACGTATGAAGAGAAGGCACTTATCGAACATCATATTTAAAGTACGAGGAG | SEQ ID NO: 99 |
| $P_{yqeZ}$-2 | CATACGTAACAAATGTATCAAAGGTTTCATTTTTTTATGTATAAAACCTGCCCTCTGCCACC | SEQ ID NO: 100 |
| $P_{ythP}$-1 | AAACTTTTTTTATTCTATTTCGTAGTAAATTTTGGAGGTGATCGAACATCATATTTAAAGTACGAGGAG | SEQ ID NO: 101 |
| $P_{ythP}$-2 | ACTACGAAATAGAATAAAAAAAGTTTCTTTAACCATAATAATATTACCTGCCCTCTGCCACC | SEQ ID NO: 102 |
| $P_{yuaF}$-1 | ACTTTTCCCGAGGTGTCTCGTATAAATGGTAACGGCAGCCGTCGAACATCATATTTAAAGTACGAGGAG | SEQ ID NO: 103 |
| $P_{yuaF}$-2 | TTTATACGAGACACCTCGGGAAAAGTTTCAAAATTTTAAGACAAAACCTGCCCTCTGCCACC | SEQ ID NO: 104 |

TABLE 3

Total fluorescence intensity of recombinant bacteria with sfGFP expression plasmids containing single promoters after culture for 24 h

| Promoter | Fluorescence intensity (a.u.) |
|---|---|
| $P_{rpoB}$ | 83184 |
| $P_{sucA}$ | 49832 |
| $P_{mtnK}$ | 3840 |
| $P_{ylbP}$ | 39028 |
| $P_{ylxM}$ | 2090 |
| $P_{yydE}$ | 13844 |
| $P_{spoVG}$ | 58281 |
| $P_{spoVS}$ | 53313 |
| $P_{spo0M}$ | 1188 |
| $P_{minC}$ | 40567 |
| $P_{sigW}$ | 17181 |
| $P_{ydbS}$ | 11706 |
| $P_{yobJ}$ | 12667 |
| $P_{yqeZ}$ | 13120 |
| $P_{ythP}$ | 4734 |
| $P_{yuaF}$ | 12260 |

Example 2: Construction and Characterization of Series Promoters

Series design is performed on $P_{rpoB}$, $P_{spoVG}$ and $P_{sigW}$. Full plasmid PCR is conducted by adopting primers in Table 5 and taking three plasmids constructed in Example 1 with promoters $P_{rpoB}$, $P_{spoVG}$ and $P_{sigW}$ as templates. Plasmids containing the series promoters and expressing sfGFP are constructed. The series promoters are named according to the type and order of series core areas, and double-series promoters $P_{AH}$, $P_{AW}$, $P_{HA}$, $P_{HW}$, $P_{AW}$, $P_{WA}$ and $P_{WH}$ (with nucleotide sequences respectively shown as SEQ ID NO:17-SEQ ID NO:22) and triple-series promoters $P_{AHW}$, $P_{AWH}$, $P_{HAW}$, $P_{HWA}$, $P_{WAH}$ and $P_{WHA}$ (with nucleotide sequences respectively shown as SEQ ID NO:23-SEQ ID NO:28) are obtained. The constructed recombinant plasmids are transformed into B. subtilis 168, and recombinant B. subtilis is obtained. The obtained recombinant B. subtilis is cultured in an LB medium at 37° C. and 200 rpm, after 6 h, 12 h and 24 h, a fluorescence signal is detected, and the degree of the activity of the promoters is judged through the intensity of the sfGFP fluorescence signal.

TABLE 5

Primers for constructing series promoters

| Primer | Sequence (5'-3')$^a$ | Sequence table number |
|---|---|---|
| $P_{rpoB-spoVG}$-1 | CGGTATTTTAACTATGTTAATA TTGTAAAATGCCAATGTATATT TTAAAAACGAGCAGGATTTCAG | SEQ ID NO: 105 |
| $P_{rpoB-sigW}$-1 | CGGTATTTTAACTATGTTAATA TTGTAAAATGCCAATGTATATT TTATAAAAAAATTGAAACCTTT TGAAAC | SEQ ID NO: 106 |
| $P_{spoVG-rpoB}$-1 | TTTCAGAAAAAATCGTGGAATT GATACACTAATGCTTTTATAAG CAAAAAAAGTTTGACTCG | SEQ ID NO: 107 |
| $P_{spoVG-sigW}$-1 | TTTCAGAAAAAATCGTGGAATT GATACACTAATGCTTTTATATT TTATAAAAAAATTGAAACCTTT TGAAACG | SEQ ID NO: 108 |
| $P_{sigW-rpoB}$-1 | ACCTTTTGAAACGAAGCTCGTA TACATACAGACCGGTGAAGAAG CAAAAAAAGTTTGACTCG | SEQ ID NO: 109 |
| $P_{sigW-spoVG}$-1 | ACCTTTTGAAACGAAGCTCGTA TACATACAGACCGGTGAAGATT TTAAAAACGAGCAGGATTTCAG | SEQ ID NO: 110 |

TABLE 6

Total fluorescence intensity of recombinant bacteria with sfGFP expression plasmids containing double-series and triple-series promoters after culture

| Primer | Fluorescence intensity (a.u.)-6 h | Fluorescence intensity (a.u.)-12 h | Fluorescence intensity (a.u.)-24 h |
|---|---|---|---|
| $P_{rpoB}$ | 12262 | 42849 | 83184 |
| $P_{spoVG}$ | 11581 | 36157 | 58281 |
| $P_{sigW}$ | 3421 | 9383 | 17181 |
| $P_{AH}$ | 20062 | 71167 | 110576 |
| $P_{AW}$ | 25264 | 53255 | 72453 |
| $P_{HA}$ | 21630 | 53088 | 76553 |
| $P_{HW}$ | 16424 | 36954 | 65127 |
| $P_{WA}$ | 5999 | 43618 | 91459 |
| $P_{WH}$ | 15518 | 60354 | 102747 |
| $P_{AHW}$ | 28506 | 61632 | 80954 |
| $P_{AWN}$ | 26367 | 76719 | 109470 |
| $P_{HAW}$ | 9267 | 44867 | 74699 |
| $P_{HWA}$ | 9830 | 49937 | 85714 |
| $P_{WAH}$ | 10261 | 71036 | 101361 |

Figure 2:
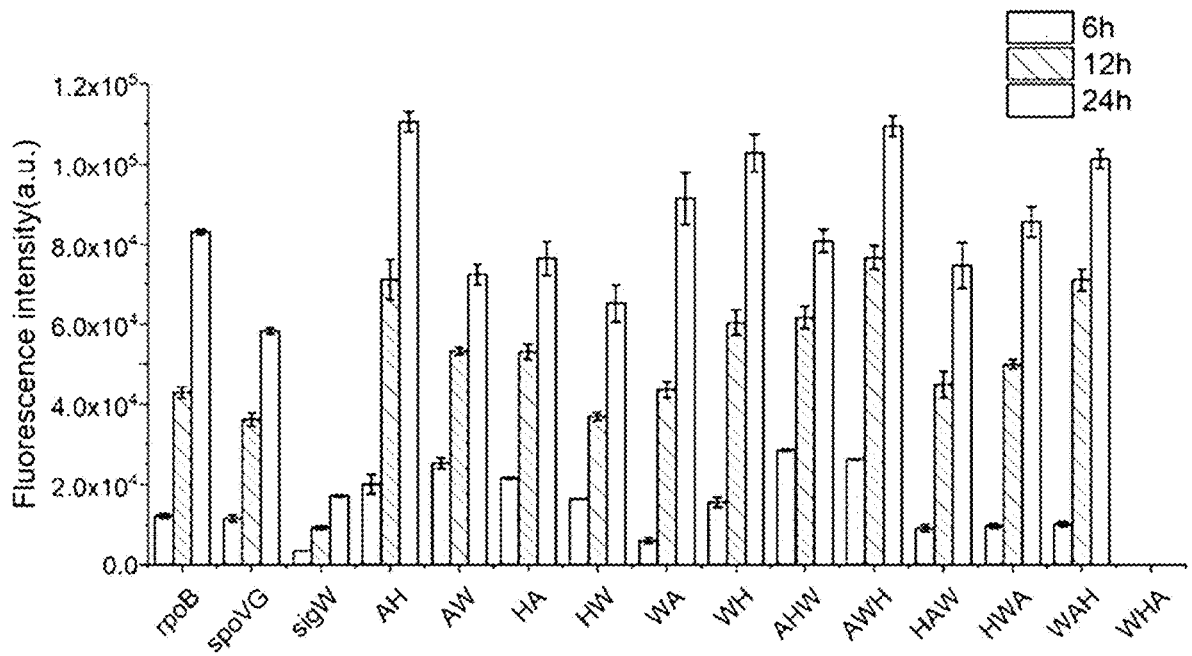
FIG. 2: construction and activity characterization of series promoters.

The fluorescence intensity of the recombinant bacteria with the sfGFP expression plasmids containing the double-series and triple-series promoters after culture for 6, 12 and 24 h is shown in FIG. 2 and Table 6. Most of the activity of the double-series promoters and the triple-series promoters is improved to different degrees compared with the activity of single promoters, and most of the activity of the triple-series promoters is higher than the activity of the double-series promoters, wherein the $P_{WHA}$ promoter plasmid is transformed into B. subtilis unsuccessfully. $P_{AH}$ with relatively high activity in the double-series promoters, and $P_{WAH}$ and $P_{AWH}$ with relatively high activity in the triple-series promoters are selected as further modification materials.

Example 3: Intervening Sequence Optimization of Series Promoters

Figure 3A:
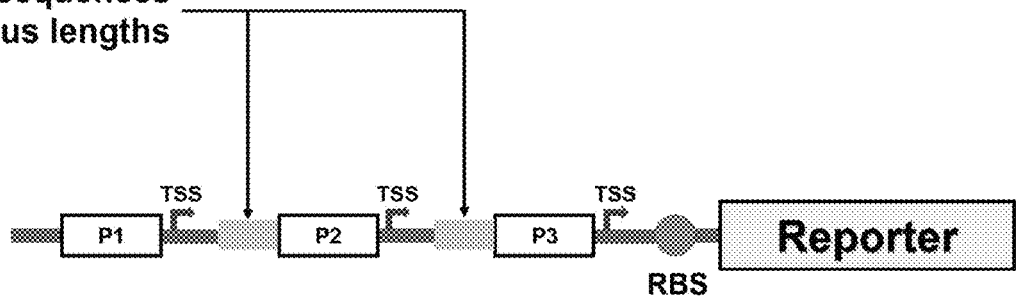
FIG. 3A: a schematic diagram of intervening sequence optimization.

Intervening sequences (FIG. 3A) of different lengths are inserted between core areas of the promoters, the lengths of the intervening sequences are set to be 15 bp, 30 bp, 45 b, 60 bp, 75 bp and 90 bp, and AH-D15, AH-D30, AH-D45, AH-D60, AH-D75, AH-D90, WAH-U15, WAH-U30, WAH-U45, WAH-U60, WAH-U75, WAH-U90, WAH-D15, WAH-D30, WAH-D45, WAH-D60, WAH-D75, WAH-D90, AWH-U15, AWH-U30, AWH-U45, AWH-U60, AWH-U75, AWH-U90, AWH-D15, AWH-D30, AWH-D45, AWH-D60, AWH-D75, AWH-D90 and AWH-DU30 (with nucleotide sequences respectively shown as SEQ ID NO:29-SEQ ID NO:59) are obtained. Promoter sequences shown as SEQ ID NO: 29-SEQ ID NO:59 are respectively cloned onto a pB-sfGFP vector. Then, recombinant plasmids are transformed into B. subtilis 168 for detection. After the obtained recombinant B. subtilis is cultured in an LB medium at 37° C. and 200 rpm for 24 h, a fluorescence signal is detected, and the degree of the activity of the promoters is judged through the intensity of the fluorescence signal of sfGFP.

The results show that for example, the fluorescence intensities of $P_{AW-D60}$ and $P_{AH-D75}$ are respectively 0.94 time and 1.03 times higher than the fluorescence intensity of $P_{AW}$ (with the fluorescence intensity of 20262 a.u/OD$_{600}$) before modification; the fluorescence intensities (18245 a.u/OD$_{600}$) of $P_{WAH-D45}$ and $P_{WAH-D75}$ are respectively 0.87 time and 0.96 time higher than the fluorescence intensity of $P_{WAH}$ (with the fluorescence intensity of 10261 a.u/OD$_{600}$) before modification; and the fluorescence intensities of $P_{AWH-D30}$ and $P_{WAH-D90}$ are respectively 0.78 time and 0.78 time higher than the fluorescence intensity of $P_{AWH}$ (with the fluorescence intensity of 16879 a.u/OD$_{600}$) before modification.

Figure 3B:
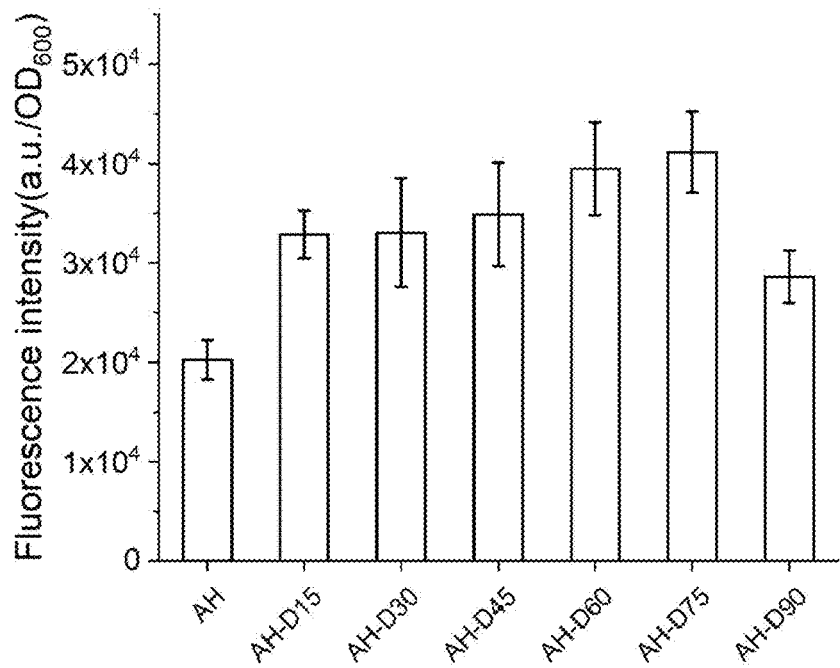
FIG. 3B: $P_{AH}$ intervening sequence optimization of core areas of promoters.
Figure 3C:
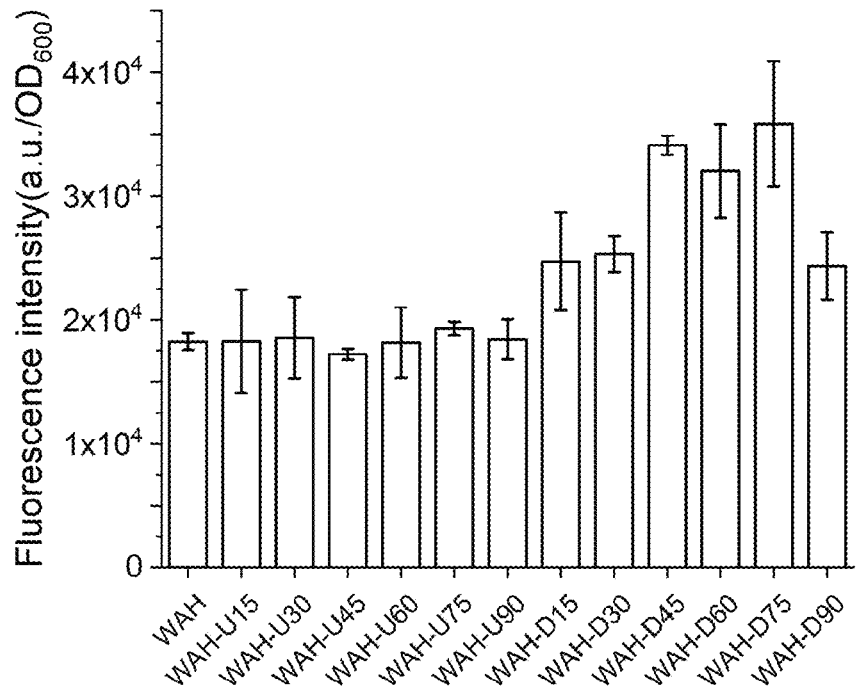
FIG. 3C: $P_{WAH}$ intervening sequence optimization of core areas of promoters.
Figure 3D:
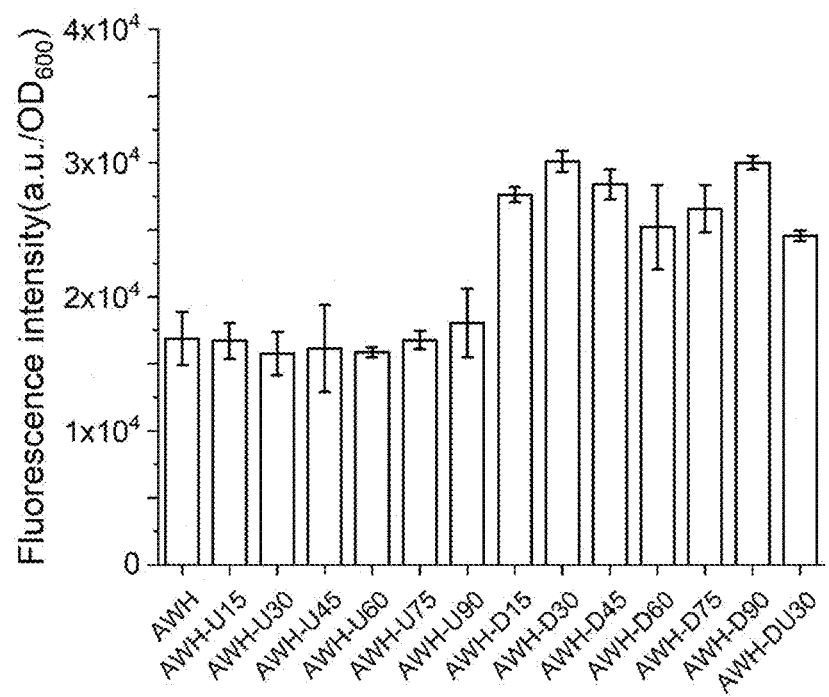
FIG. 3D: $P_{AWH}$ intervening sequence optimization of core areas of promoters.
Figure 4A:
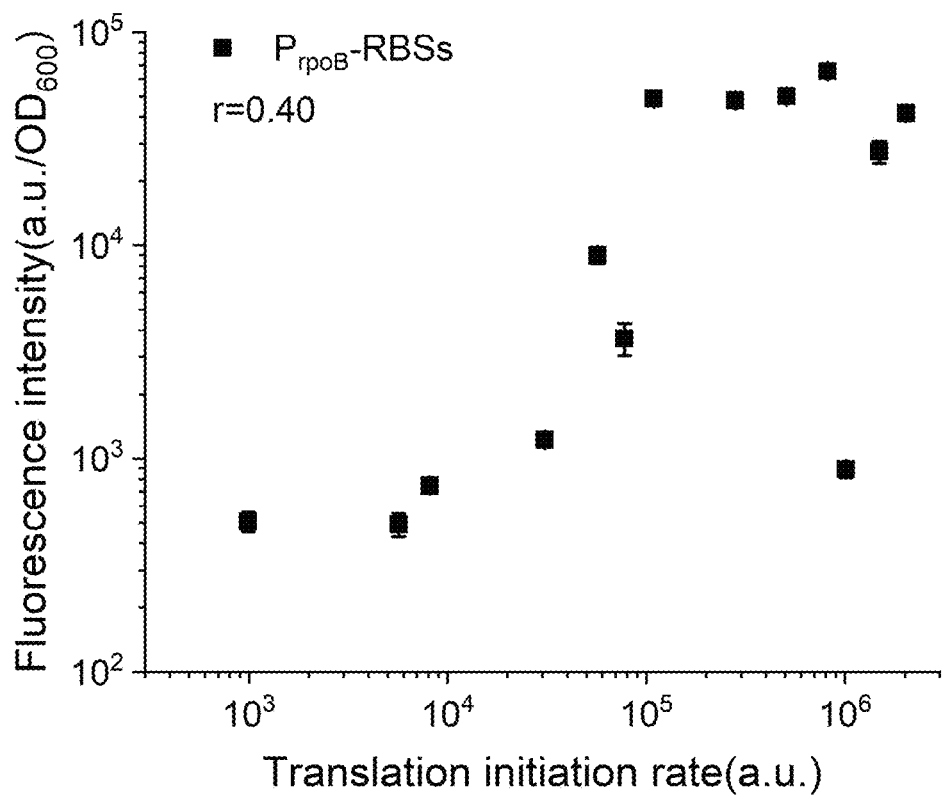
FIG. 4A: compatibility detection of $P_{rpoB}$ promoter with an RBS
Figure 4B:
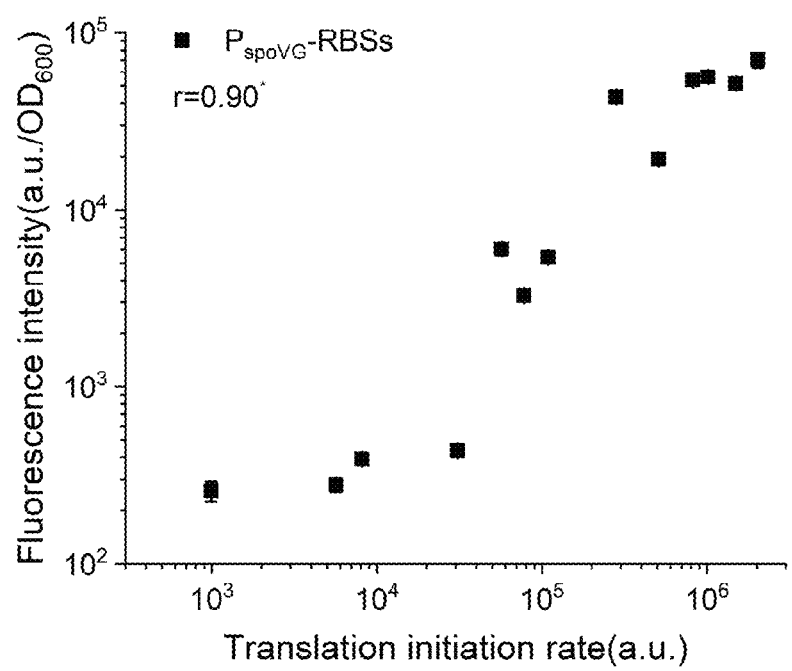
FIG. 4B compatibility detection of $P_{spoVG}$ promoter with an RBS.
Figure 4C:
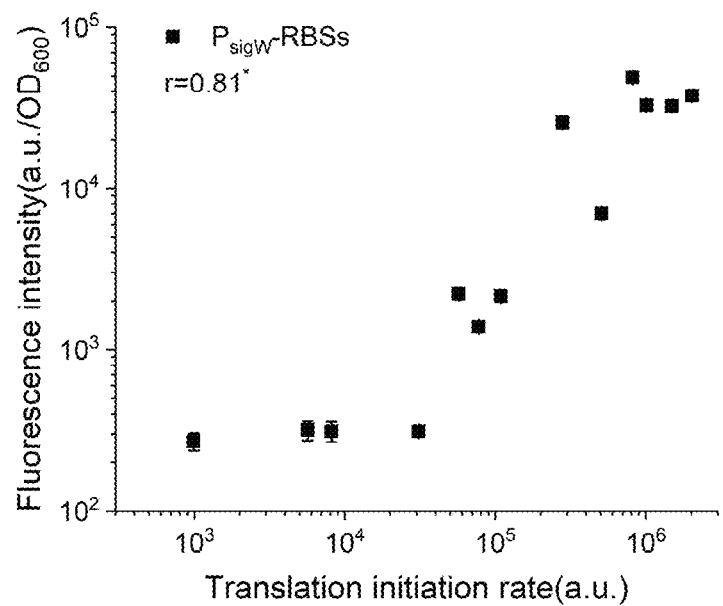
FIG. 4C compatibility detection of $P_{sigW}$ promoter with an RBS.
Figure 4D:
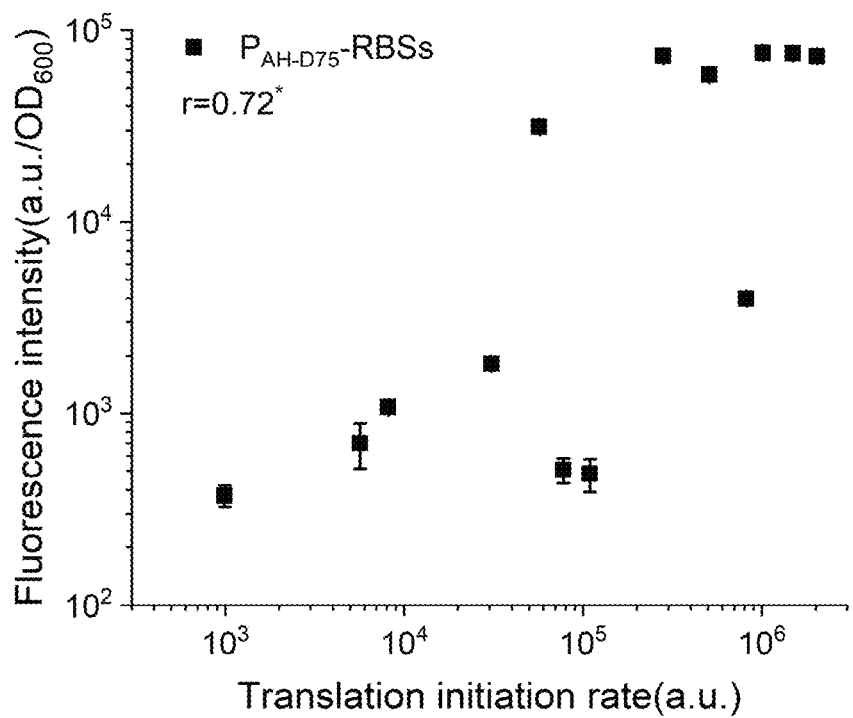
FIG. 4D compatibility detection of $P_{AH-D75}$ promoter with an RBS.
Figure 4E:
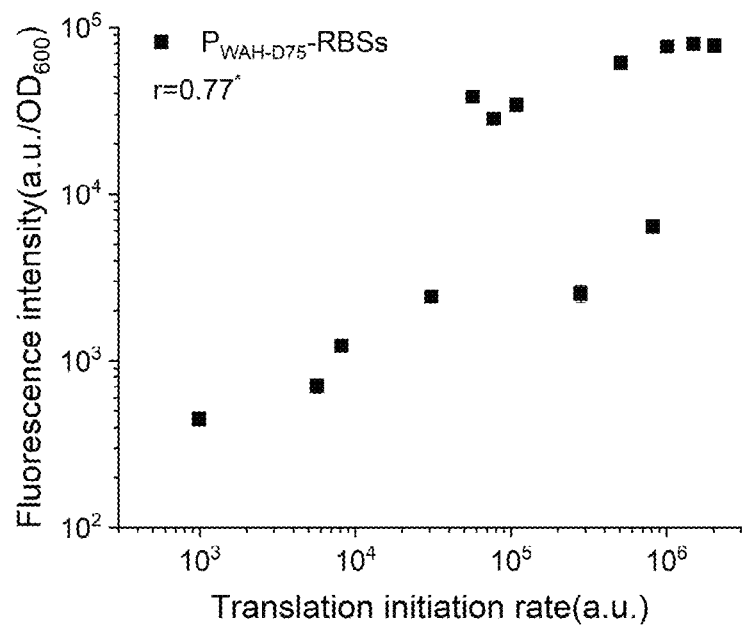
FIG. 4E compatibility detection of $P_{WAH-D75}$ promoter with an RBS.
Figure 4F:
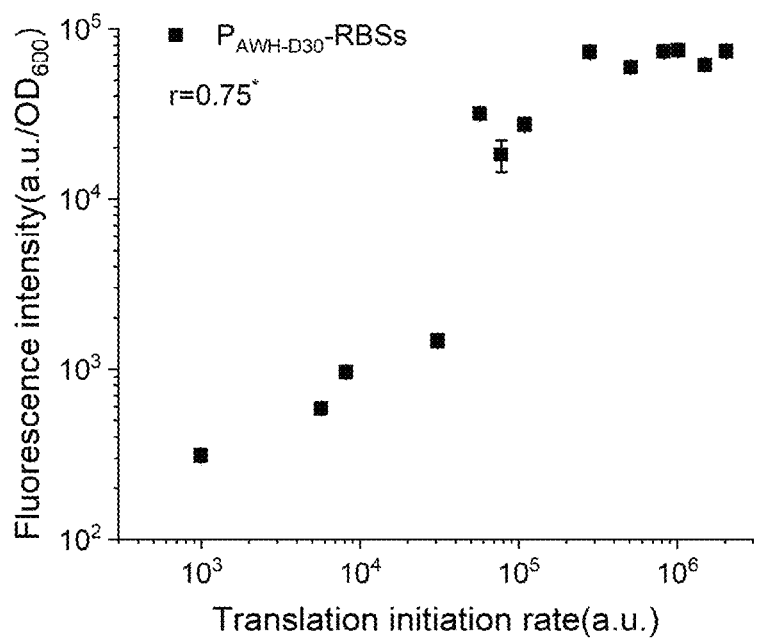
FIG. 4F compatibility detection of $P_{AWH-D30}$ promoter with an RBS.

(FIGS. 3B, 3C and 3D; and Table 8). The result shows that the activity of the series promoters can be further effectively improved by inserting the intervening sequences of the proper lengths between the series core areas.

TABLE 7

Fluorescence intensity of recombinant bacteria of recombinant plasmids of double-series and triple-series promoters containing inserted intervening sequences after culture for 24 h

| Promoter | Fluorescence intensity (a.u./OD$_{600}$) |
|---|---|
| $P_{AH}$ | 20262 |
| $P_{AH-D15}$ | 32865 |
| $P_{AH-D30}$ | 33033 |
| $P_{AH-D45}$ | 34869 |
| $P_{AH-D60}$ | 39476 |
| $P_{AH-D75}$ | 41154 |
| $P_{AH-D90}$ | 28592 |
| $P_{WAH}$ | 18245 |
| $P_{WAH-U15}$ | 18278 |
| $P_{WAH-U30}$ | 18553 |
| $P_{WAH-U45}$ | 17198 |

TABLE 7-continued

Fluorescence intensity of recombinant bacteria of recombinant plasmids of double-series and triple-series promoters containing inserted intervening sequences after culture for 24 h

| Promoter | Fluorescence intensity (a.u./OD$_{600}$) |
|---|---|
| P$_{WAH-U60}$ | 18161 |
| P$_{WAH-U75}$ | 19295 |
| P$_{WAH-U90}$ | 18419 |
| P$_{WAH-D15}$ | 24711 |
| P$_{WAH-D30}$ | 25307 |
| P$_{WAH-D45}$ | 34100 |
| P$_{WAH-D60}$ | 32029 |
| P$_{WAH-D75}$ | 35819 |
| P$_{WAH-D90}$ | 24355 |
| P$_{AWH}$ | 16879 |
| P$_{AWH-U15}$ | 16707 |
| P$_{AWH-U30}$ | 15762 |
| P$_{AWH-U45}$ | 16157 |
| P$_{AWH-U60}$ | 15852 |
| P$_{AWH-U75}$ | 16770 |
| P$_{AWH-U90}$ | 18045 |
| P$_{AWH-D15}$ | 27627 |
| P$_{AWH-D30}$ | 30084 |
| P$_{AWH-D45}$ | 28409 |
| P$_{AWH-D60}$ | 25195 |
| P$_{AWH-D75}$ | 26580 |
| P$_{AWH-D90}$ | 29999 |
| P$_{AWH-DU30}$ | 24562 |

Example 4: Compatibility Research of Promoters and RBSs

The promoters P$_{rpoB}$, P$_{spoVG}$, P$_{sigW}$, P$_{AH-D75}$, P$_{WAH-D75}$ and P$_{AWH-D30}$ in Example 1 and Example 3 are respectively combined with 13 RBSs. RBS1-13 sequences (with nucleotide sequences respectively shown as SEQ ID NO:60-SEQ ID NO:72) are respectively cloned onto a vector containing series promoters. Then, recombinant plasmids are transformed into *B. subtilis* 168. After the obtained recombinant *B. subtilis* is cultured in an LB medium at 37° C. and 200 rpm for 24 h, a fluorescence signal is detected, and the degree of the activity of the promoters is judged through the intensity of the fluorescence signal of sfGFP. Then, correlation analysis is performed on RBS theoretical intensities of different combinations and actually-measured fluorescence values, and correlations are evaluated through r values. The result is shown in FIG. 4A-4F, the correlation of single promoter P$_{ropB}$ and RBS combined design is low, while each of the correlations after the series promoters and the RBSs are combined is higher than combination of the single promoter Props and the RBSs, which shows that the compatibility of combined use of the promoters and RBS elements can be improved through the design of the RBSs by the series promoters, that is, the designability and predictability during exogenous protein expression are enhanced.

As shown in Table 8, when P$_{AH-D75}$ is combined with RBS11 (SEQ ID NO:70), the fluorescence intensity can reach 76216 a.u/OD$_{600}$ and is 0.85 time higher than that of P$_{AH-D75}$; when P$_{WAH-D75}$ is combined with RBS13 (SEQ ID NO:72), the fluorescence intensity can reach 77751 a.u/OD$_{600}$ and is 1.17 times higher than that of P$_{WAH-D75}$; and when P$_{AWH-D30}$ is combined with RBS13 (SEQ ID NO:72), the fluorescence intensity can reach 73781 a.u/OD$_{600}$ and is 1.45 times higher than that of P$_{AWH-D30}$. It shows that the expression of a target gene can be further enhanced through the design of the RBSs by the series promoters.

TABLE 8

Translation initiation rate and fluorescence intensity after respective combination of promoters with RBS1-13

| Promoter | RBS | Translation initiation rate (a.u.) | Fluorescence intensity (a.u./OD$_{600}$) |
|---|---|---|---|
| P$_{rpoB-}$ | RBS1 | 993 | 506 |
| | RBS2 | 5675 | 490 |
| | RBS3 | 8164 | 744 |
| | RBS4 | 30770 | 1224 |
| | RBS5 | 56900 | 8983 |
| | RBS6 | 77621 | 3665 |
| | RBS7 | 109196 | 48675 |
| | RBS8 | 280412 | 47717 |
| | RBS9 | 507918 | 50055 |
| | RBS10 | 818340 | 65439 |
| | RBS11 | 1011200 | 892 |
| | RBS12 | 1489100 | 27493 |
| | RBS13 | 2031360 | 41641 |
| P$_{spoVG-}$ | RBS1 | 993 | 258 |
| | RBS2 | 5675 | 279 |
| | RBS3 | 8164 | 390 |
| | RBS4 | 30770 | 434 |
| | RBS5 | 56900 | 6024 |
| | RBS6 | 77621 | 3272 |
| | RBS7 | 109196 | 5417 |
| | RBS8 | 280412 | 43386 |
| | RBS9 | 507918 | 19364 |
| | RBS10 | 818340 | 53879 |
| | RBS11 | 1011200 | 56203 |
| | RBS12 | 1489100 | 51777 |
| | RBS13 | 2031360 | 70532 |
| P$_{sigW-}$ | RBS1 | 993 | 270 |
| | RBS2 | 5675 | 317 |
| | RBS3 | 8164 | 312 |
| | RBS4 | 30770 | 312 |
| | RBS5 | 56900 | 2213 |
| | RBS6 | 77621 | 1385 |
| | RBS7 | 109196 | 2142 |
| | RBS8 | 280412 | 25573 |
| | RBS9 | 507918 | 6991 |
| | RBS10 | 818340 | 48885 |
| | RBS11 | 1011200 | 32878 |
| | RBS12 | 1489100 | 32409 |
| | RBS13 | 2031360 | 37704 |
| P$_{AH-D75-}$ | RBS1 | 993 | 373 |
| | RBS2 | 5675 | 700 |
| | RBS3 | 8164 | 1078 |
| | RBS4 | 30770 | 1822 |
| | RBS5 | 56900 | 31182 |
| | RBS6 | 77621 | 506 |
| | RBS7 | 109196 | 484 |
| | RBS8 | 280412 | 73457 |
| | RBS9 | 507918 | 58264 |
| | RBS10 | 818340 | 3976 |
| | RBS11 | 1011200 | 76216 |
| | RBS12 | 1489100 | 75723 |
| | RBS13 | 2031360 | 73351 |
| P$_{WAH-D75-}$ | RBS1 | 993 | 447 |
| | RBS2 | 5675 | 704 |
| | RBS3 | 8164 | 1229 |
| | RBS4 | 30770 | 2416 |
| | RBS5 | 56900 | 38253 |
| | RBS6 | 77621 | 28222 |
| | RBS7 | 109196 | 34329 |
| | RBS8 | 280412 | 2539 |
| | RBS9 | 507918 | 60937 |
| | RBS10 | 818340 | 6350 |
| | RBS11 | 1011200 | 76533 |
| | RBS12 | 1489100 | 79375 |
| | RBS13 | 2031360 | 77751 |

TABLE 8-continued

Translation initiation rate and fluorescence intensity after respective combination of promoters with RBS1-13

| Promoter | RBS | Translation initiation rate (a.u.) | Fluorescence intensity (a.u./OD$_{600}$) |
| --- | --- | --- | --- |
| P$_{AWH\text{-}D30\text{-}}$ | RBS1 | 993 | 310 |
| | RBS2 | 5675 | 590 |
| | RBS3 | 8164 | 960 |
| | RBS4 | 30770 | 1465 |
| | RBS5 | 56900 | 31627 |
| | RBS6 | 77621 | 18187 |
| | RBS7 | 109196 | 27310 |
| | RBS8 | 280412 | 73026 |
| | RBS9 | 507918 | 59282 |
| | RBS10 | 818340 | 73459 |
| | RBS11 | 1011200 | 74559 |
| | RBS12 | 1489100 | 61201 |
| | RBS13 | 2031360 | 73781 |

Although the present disclosure has been disclosed as above as exemplary examples, it is not intended to limit the present disclosure. Any of those skilled in the art may make various alterations and modifications without departing from the spirit and scope of the present disclosure. Therefore, the protection scope of the present disclosure shall be as defined in the claims.

What is claimed is:

1. A method for regulating and controlling target gene expression, comprising co-expressing a recombinant DNA element as a regulating and controlling element to regulate and control expression of a target gene, wherein the regulating and controlling element is co-expressed with the target gene and comprises an artificial series promoter and a downstream ribosome binding site (RBS) thereof, wherein the artificial series promoter is formed by connecting at least two promoters selected from the group consisting of $P_{rpoB}$, $P_{spoVG}$ and $P_{sigW}$ in series and nucleotide sequences of the promoters $P_{rpoB}$, $P_{spoVG}$ and $P_{sigW}$ are set forth as SEQ ID NO:1, SEQ ID NO:7 and SEQ ID NO:11, respectively.

2. The method according to claim 1, wherein the nucleotide sequence of the artificial series promoter is set forth as any one of SEQ ID NO: 17-27.

3. The method according to claim 1, wherein the nucleotide sequence of the artificial series promoter is set forth as any one of SEQ ID NO: 29-59.

4. The method according to claim 1, wherein the nucleotide sequence of the RBS is set forth as any one of SEQ ID NO:60-72.

5. The method according to claim 1, wherein intervening sequences of 60 bp and 75 bp are inserted between the promoters $P_{rpoB}$ and $P_{spoVG}$, respectively, to obtain new promoters $P_{AW-D60}$ and $P_{AH-D75}$ set forth as SEQ ID NO:32 and SEQ ID NO:33, respectively.

6. The method according to claim 1, wherein intervening sequences of 45 bp and 75 bp are inserted between the first two promoters $P_{sigW}$, $P_{rpoB}$ and $P_{spoVG}$, respectively, to obtain new promoters $P_{WAH-D45}$ and $P_{WAH-D75}$ set forth as SEQ ID NO: 43 and SEQ ID NO:45, respectively.

7. The method according to claim 1, wherein intervening sequences of 30 bp and 90 bp are inserted between the first two promoters $P_{rpoB}$, $P_{sigW}$ and $P_{spoVG}$, respectively, to obtain new promoters $P_{AWH-D30}$ and $P_{WAH-D90}$ set forth as SEQ ID NO: 54 and SEQ ID NO:58, respectively.

8. The method according to claim 1, wherein the nucleotide sequence of the artificial series promoter is set forth as any one of SEQ ID NO:17-27 and SEQ ID NO: 29-59; and a nucleotide sequence of the RBS is set forth as any one of SEQ ID NO:60-72.

9. The method according to claim 8, wherein an expression host of the target gene comprises *Bacillus subtilis*.

10. The method according to claim 9, wherein the expression host of the target gene comprises *Bacillus subtilis* (*B. subtilis*) 168, *B. subtilis* WB400, *B. subtilis* WB600 or *B. subtilis* WB800.

11. The method according to claim 1, wherein the target gene comprises an exogenous gene.

12. The method according to claim 1, wherein the target gene comprises an endogenous gene.

13. The method according to claim 1, wherein the target gene comprises an enzyme gene or a non-enzyme gene.

14. The method according to claim 1, wherein the method is applied to a field of food, health care products or pharmaceuticals.

15. A recombinant DNA element for regulating and controlling gene expression, comprising an artificial series promoter and a downstream RBS thereof, wherein the artificial series promoter is formed by connecting at least two promoters selected from the group consisting of $P_{rpoB}$, $P_{spoVG}$ and $P_{sigW}$ in series and wherein nucleotide sequences of the promoters $P_{rpoB}$, $P_{spoVG}$ and $P_{sigW}$ are set forth as SEQ ID NO:1, SEQ ID NO:7 and SEQ ID NO: 11, respectively.

16. A genetic engineering bacterium for expressing the recombinant DNA element according to claim 15.

* * * * *